(12) United States Patent
Toba et al.

(10) Patent No.: US 12,664,645 B2
(45) Date of Patent: Jun. 23, 2026

(54) CELL IMAGE ANALYSIS METHOD FOR DETECTING COLONY CHANGE POINTS AND NON-TRANSITORY STORAGE MEDIUM

(71) Applicant: CANON KABUSHIKI KAISHA, Tokyo (JP)

(72) Inventors: Shuhei Toba, Kanagawa (JP); Yoji Yamamoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 679 days.

(21) Appl. No.: 18/165,356

(22) Filed: Feb. 7, 2023

(65) Prior Publication Data

US 2023/0252630 A1 Aug. 10, 2023

(30) Foreign Application Priority Data

Feb. 10, 2022 (JP) ................................. 2022-019604
Sep. 8, 2022 (JP) ................................. 2022-143150

(51) Int. Cl.
| | |
|---|---|
| *G06T 7/00* | (2017.01) |
| *C12M 1/34* | (2006.01) |
| *C12M 1/36* | (2006.01) |
| *G06T 7/62* | (2017.01) |
| *G06V 10/25* | (2022.01) |

(52) U.S. Cl.
CPC ........... *G06T 7/0012* (2013.01); *C12M 41/36* (2013.01); *C12M 41/48* (2013.01); *G06T 7/62* (2017.01); *G06V 10/25* (2022.01); *G06T 2207/30024* (2013.01)

(58) Field of Classification Search
CPC ..................... G06T 7/0012; G06T 7/62; G06T 2207/30024; G06T 7/0016; C12M 41/36; C12M 41/48; C12M 47/04; G06V 10/25; G06V 20/693; G06V 20/695
See application file for complete search history.

(56) References Cited

U.S. PATENT DOCUMENTS

| | | | |
|---|---|---|---|
| 2012/0122143 A1 | 5/2012 | Mimura et al. | |
| 2016/0163049 A1* | 6/2016 | Matsubara | G06V 20/695 |
| | | | 382/133 |
| 2016/0370569 A1* | 12/2016 | Matsumoto | G01N 15/1433 |
| 2021/0010054 A1 | 1/2021 | Uchiho et al. | |
| 2021/0292703 A1 | 9/2021 | Dan et al. | |

FOREIGN PATENT DOCUMENTS

| | | |
|---|---|---|
| JP | 2009044974 A | 3/2009 |
| JP | 2016123366 A | 7/2016 |
| WO | 2011013319 A1 | 2/2011 |

* cited by examiner

*Primary Examiner* — Kent Yip
(74) *Attorney, Agent, or Firm* — Carter, DeLuca & Farrell LLP

(57) ABSTRACT

Provided is a cell image analysis method which enables accurate grasping of a change point of a colony in cell culture. The cell image analysis method includes: a data acquisition step of acquiring cell image data generated in time series in the cell culture; a cell region extraction step of extracting cell regions from the cell image data; a data calculation step of calculating, for each of the cell regions, data about a size of the cell region; and a change point detection step of detecting, based on the data about the size of the cell region calculated in the data calculation step, the change point, which is timing of a change in a state of the colony.

17 Claims, 22 Drawing Sheets

S301 — GENERATE DIFFERENTIAL IMAGE

S302 — EXECUTE BINARIZATION PROCESSING

S303 — GENERATE MASK IMAGE OF CELL REGION

S304 — EXECUTE LABELING PROCESSING

FIG. 4
401
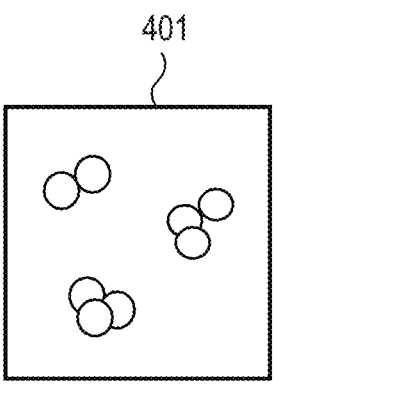
402
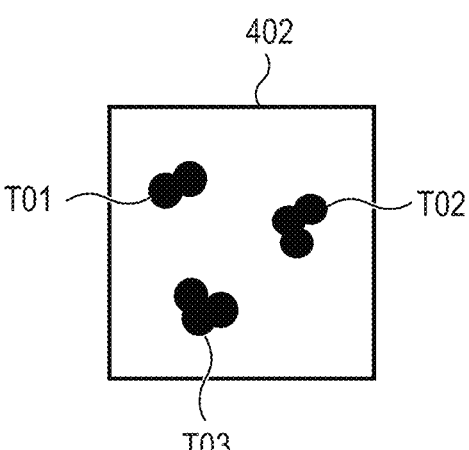

FIG. 8

| CELL REGION NUMBER | RADIUS [μm] | LENGTH OF CULTURE TIME [day] |
|---|---|---|
| 1 | 610.95 | 6.2 |
| 2 | 573.98 | 6.0 |
| 3 | 723.74 | 7.0 |
| | . | |
| | . | |
| | . | |

FIG. 10 i-TH PASSAGE (i+1)TH PASSAGE

Figure 10:
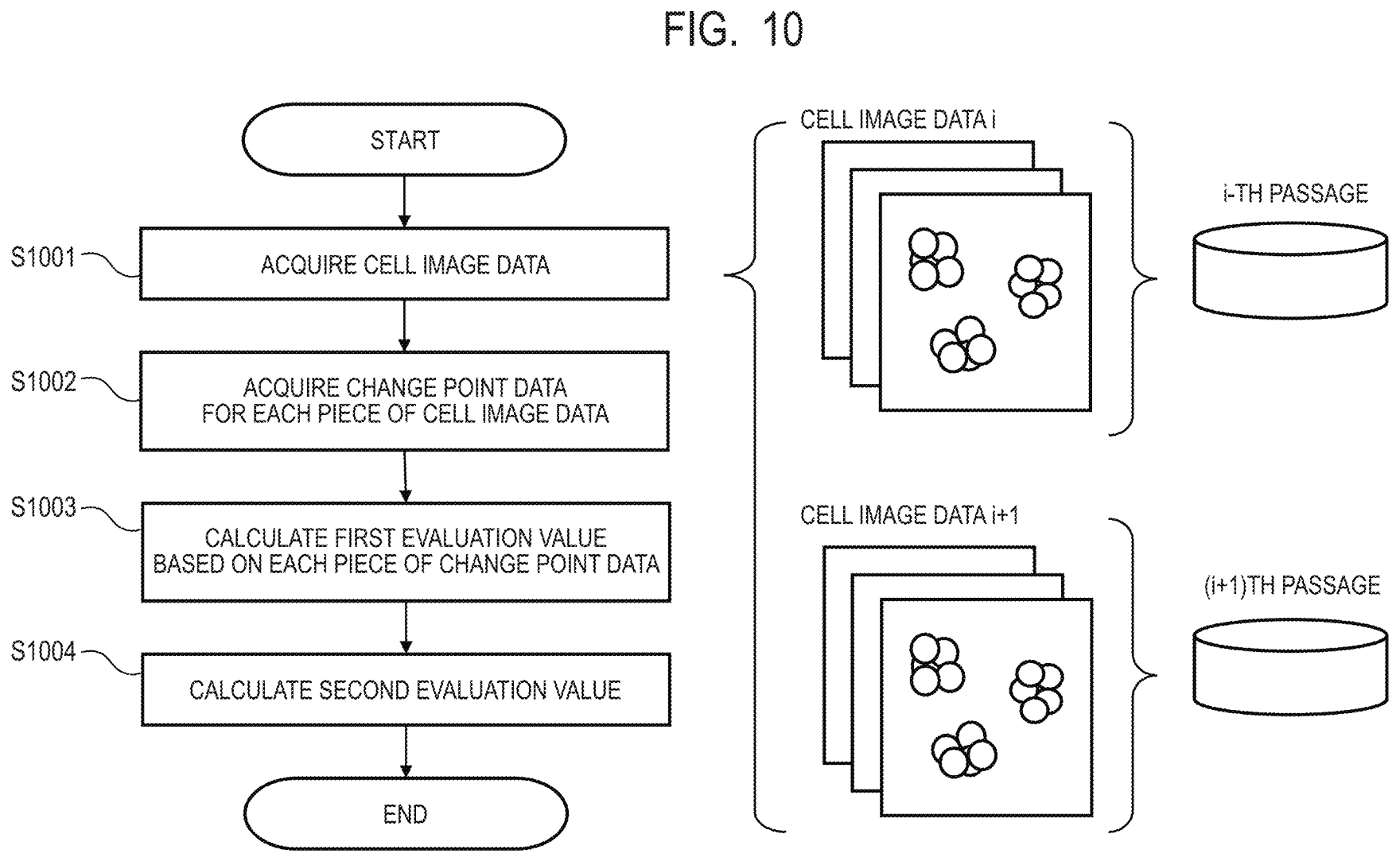

CELL IMAGE DATA i

CELL IMAGE DATA i+1

START

ACQUIRE CELL IMAGE DATA — S1001

ACQUIRE CHANGE POINT DATA FOR EACH PIECE OF CELL IMAGE DATA — S1002

CALCULATE FIRST EVALUATION VALUE BASED ON EACH PIECE OF CHANGE POINT DATA — S1003

CALCULATE SECOND EVALUATION VALUE — S1004

END

| | | CULTURE CONDITIONS | | | | | |
| --- | --- | --- | --- | --- | --- | --- | --- |
| | | 1/4 SEEDING DENSITY MEDIUM QUANTITY :1.0 ML | 1/4 SEEDING DENSITY MEDIUM QUANTITY :2.0 ML | 1/4 SEEDING DENSITY MEDIUM QUANTITY :4.0 ML | EQUAL SEEDING DENSITY MEDIUM QUANTITY :1.0 ML | EQUAL SEEDING DENSITY MEDIUM QUANTITY :2.0 ML | EQUAL SEEDING DENSITY MEDIUM QUANTITY :4.0 ML |
| COLONY COUNT | | 938 | 928 | 759 | 185 | 190 | 121 |
| STATISTICS OF COLONY DIAMETER AT CHANGE POINT | AVERAGE | 320.77 | 362.85 | 396.51 | 279.57 | 294.91 | 333.31 |
| | STANDARD DEVIATION | 61.03 | 69.65 | 69.39 | 45.82 | 67.30 | 62.17 |
| | CV VALUE | 0.19 | 0.19 | 0.18 | 0.16 | 0.23 | 0.19 |
| | MINIMUM VALUE | 190.75 | 175.79 | 171.86 | 190.17 | 196.42 | 205.12 |
| | 25 PERCENTILE | 283.18 | 315.15 | 349.12 | 247.97 | 251.59 | 286.41 |
| | MEDIAN VALUE | 310.61 | 355.32 | 394.39 | 269.80 | 277.35 | 327.78 |
| | 75 PERCENTILE | 347.48 | 407.22 | 443.83 | 301.27 | 316.70 | 381.52 |
| | MAXIMUM VALUE | 776.06 | 704.76 | 682.97 | 490.43 | 660.12 | 452.33 |

CELL IMAGE ANALYSIS METHOD FOR DETECTING COLONY CHANGE POINTS AND NON-TRANSITORY STORAGE MEDIUM

BACKGROUND OF THE INVENTION

Field of the Invention

The present invention relates to a cell image analysis method and a non-transitory storage medium.

Description of the Related Art

In cell culture, a worker observes appearance of cells and subjectively determines timing of cell processing in many cases. This is one of factors that diminish reproducibility and stability of cell culture, and, in order to ensure reproducibility and stability, an objective determination method independent of the worker's subjective view is wanted. In a case of adherent cells, a method in which a culture vessel is successively observed and next cell processing is executed at a time when a confluence (an area ratio of cells to the culture vessel) exceeds a value determined in advance is often adopted.

The method of determining timing of cell processing based on the confluence is very effective for cells that do not form a colony and are cultured in a state in which individual cells are separated from one another. However, in a case of ES cells, iPS cells, and other cells that form a colony, a cell-to-cell interaction that takes place in each individual colony is considered to affect states of the cells. For that reason, in order to improve reproducibility and stability of culture, it is desired to determine timing of cell processing by objectively grasping, for each colony, timing at which the state of the colony changes (hereinafter referred to as "change point"), instead of using the confluence.

In International Publication No. WO2011/013319, there is thus proposed determination of the degree of maturity of a cell aggregation based on time lapse changes in calculated degree of multi-layering of cells. The degree of multi-layering here is an index calculated from a feature related to texture of cells.

In International Publication No. WO2011/013319, there is also proposed grasping of timing of colony differentiation by determining whether a colony is differentiated or undifferentiated based on a plurality of image feature values, and capturing time lapse changes thereof.

However, in observation of an image of a colony, defocusing of an observation apparatus and superimposition of a large number of dead cells on the colony frequently happen. Accordingly, there is a case in which it is difficult to accurately grasp the change point of the colony based on texture of the image as in International Publication No. WO2011/013319.

SUMMARY OF THE INVENTION

The present invention has been made to solve the problem described above. That is, an object of the present invention is to provide a cell image analysis method which enables accurate grasping of a change point of a colony in cell culture.

According one aspect of the present invention, there is provided a cell image analysis method including: a data acquisition step of acquiring cell image data generated in time series in cell culture; a cell region extraction step of extracting, from the cell image data, a plurality of cell regions where one cell region corresponds to one of a plurality of colonies; a data calculation step of calculating, for each of the plurality of cell regions, data about a size of the each of the plurality of cell regions; and a change point detection step of detecting, based on the size of the each of the plurality of cell regions calculated in the data calculation step, a change point, which is timing of a change in a state of each of the plurality of colonies.

According another aspect of the present invention, there is provided a non-transitory storage medium storing a program for causing a computer to execute the above-mentioned cell image analysis method.

Further features of the present invention will become apparent from the following description of exemplary embodiments with reference to the attached drawings.

BRIEF DESCRIPTION OF THE DRAWINGS

FIG. 4 is a diagram for illustrating an example of the cell regions extracted in Step S102 in the first embodiment.

FIG. 8 is a table for showing an example of data of the change point in Step S104 in the first embodiment.

FIG. 10 is a flow chart of a cell image analysis method according to a third embodiment.

FIG. 14 is a graph for showing results of comparing distributions of colony diameters at change points depending on a seeding density and on a medium quantity.

FIG. 17 is a graph for showing results of comparing distributions of rates at which the area changes at change points depending on the coating density.

FIG. 20 is a table for showing an example of statistics of distributions of colony diameters at change points depending on culture conditions.

DESCRIPTION OF THE EMBODIMENTS

Now, referring to the accompanying drawings, embodiments of the present invention are described. The present invention is not limited to the following embodiments.

First Embodiment

In a first embodiment, a method of detecting a change point of a cell region from time-series cell images is described by taking a stem cell as a favorable example of a cell that forms a cell colony (hereinafter simply referred to as "colony"). Examples of the stem cell that can be used include an induced pluripotent stem cell (iPS cell), an embryonic stem cell (ES cell), and a mesenchymal stem cell. "Colonies" in the first embodiment refer to communities each of which is made up of cells in contact with one another and each of which is an independent presence in a culture vessel (hereinafter simply referred to as "cell community"). That is, a cell community unbonded to surroundings is regarded as one colony. The present invention has a feature of detecting a change point for each of cell communities by discriminating the cell communities from one another where the cell communities are present independently from one another in a culture vessel, instead of detecting a change point for an entire cell community in the culture vessel.

Figure 1:
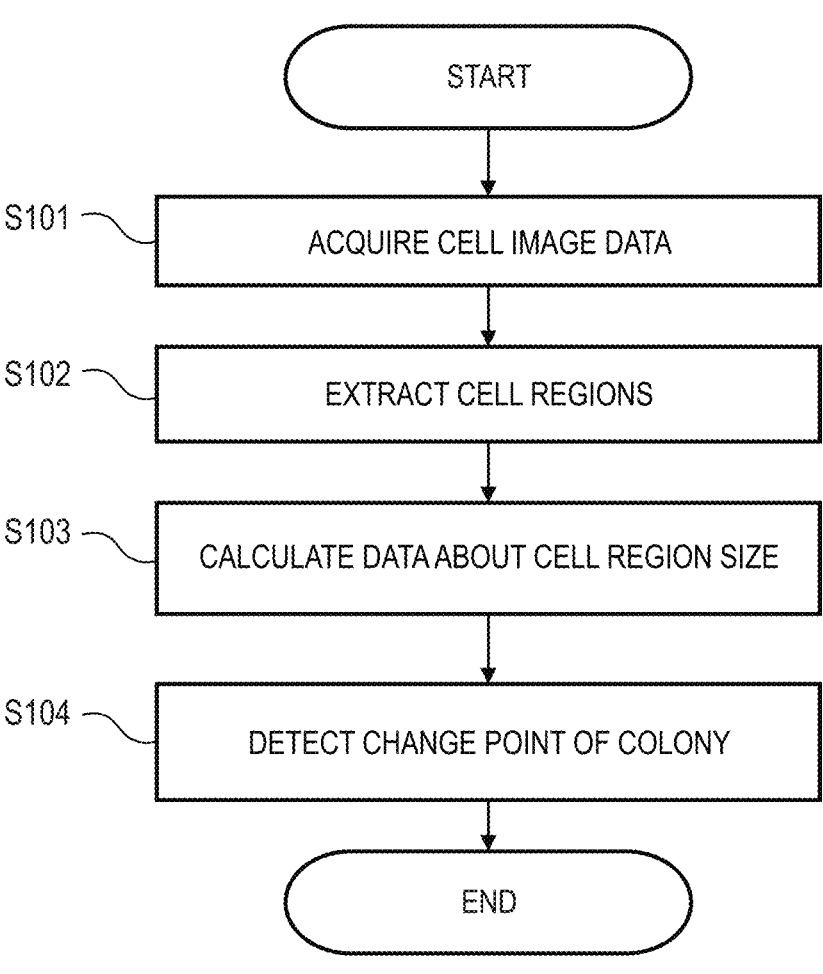
FIG. 1 is a flow chart of a cell image analysis method according to a first embodiment.

FIG. 1 is a flow chart of a cell image analysis method according to the first embodiment.

Step S101 is a data acquisition step of acquiring cell image data generated in time series in cell culture. The data acquisition step may include acquisition of cell image data generated in time series in cell culture in which an undifferentiated state is maintained. In Step S101, cell image data acquired by a cell culture observation apparatus is acquired. Here, the cell image data is data of time-series phase contrast images acquired at a predetermined time interval for a fixed length of period in one culture vessel. "Cell image" or simple "image" hereinafter refers to a phase contrast image. Here, the cell image data may be one acquired in real time from the cell culture observation apparatus, or one acquired from an external storage area such as an HDD or cloud storage.

In culture of a stem cell, it is found through detailed analysis of appearance of colony growth that there is timing at which a rate of colony growth changes from an increase trend to a decrease trend, that is, timing (a change point) at which the rate of change in area of a cell region changes from increase to decrease. Specifically, a stem cell starts to form colonies approximately two days from seeding, and some of the colonies slow down in growth rate around Day 6. Accordingly, the above-mentioned fixed length of period is preferred to be a period starting at a time point selected from time points of Day 2 or earlier and ending at a time point selected from time points of Day 7 or later. The time interval at which an image is acquired is set to, for example, 6 hours. In the present invention, a concept of timing at which the rate of colony growth changes from an increase trend to a decrease trend is referred to as "change point." The change point is referred to as "growth suppression point" in some places. A specific index indicating the change point is not limited to a particular variable. For example, the length of culture time or a size of a cell region is usable as a variable that serves as a specific index indicating the change point, as described later.

As described later, the inventors of the present invention have found out that, when there are a plurality of colonies, the timing (change point) at which the rate of change in area of a cell region changes from increase to decrease varies from colony to colony. Accordingly, when subsequent cell processing (passage and the like) is performed based on detection of the change point of a specific colony alone, there may be a case in which cell growth is insufficient (halfway through growth), or a case in which cells have fully grown but colonies slow in growth rate are included. It is accordingly considered that colony-by-colony cell processing can be executed at appropriate timing by detecting the change point for each colony. It is also considered that more appropriate culture conditions can be set based on current culture conditions and information about the change point of each colony.

The time interval at which an image is acquired may be set so that data is acquired at a long time interval prior to a period that may include the change point, and at a short time interval after this period starts. In that case, image data may be acquired by setting the interval to, for example, every 12 hours on days prior to Day 2 of culture and from Day 2 to Day 5, and every 4 hours on Day 5 and subsequent days. An example of the image data that can be used is image data acquired by a cell image observation apparatus such as Incucyte S3.

Figure 2:
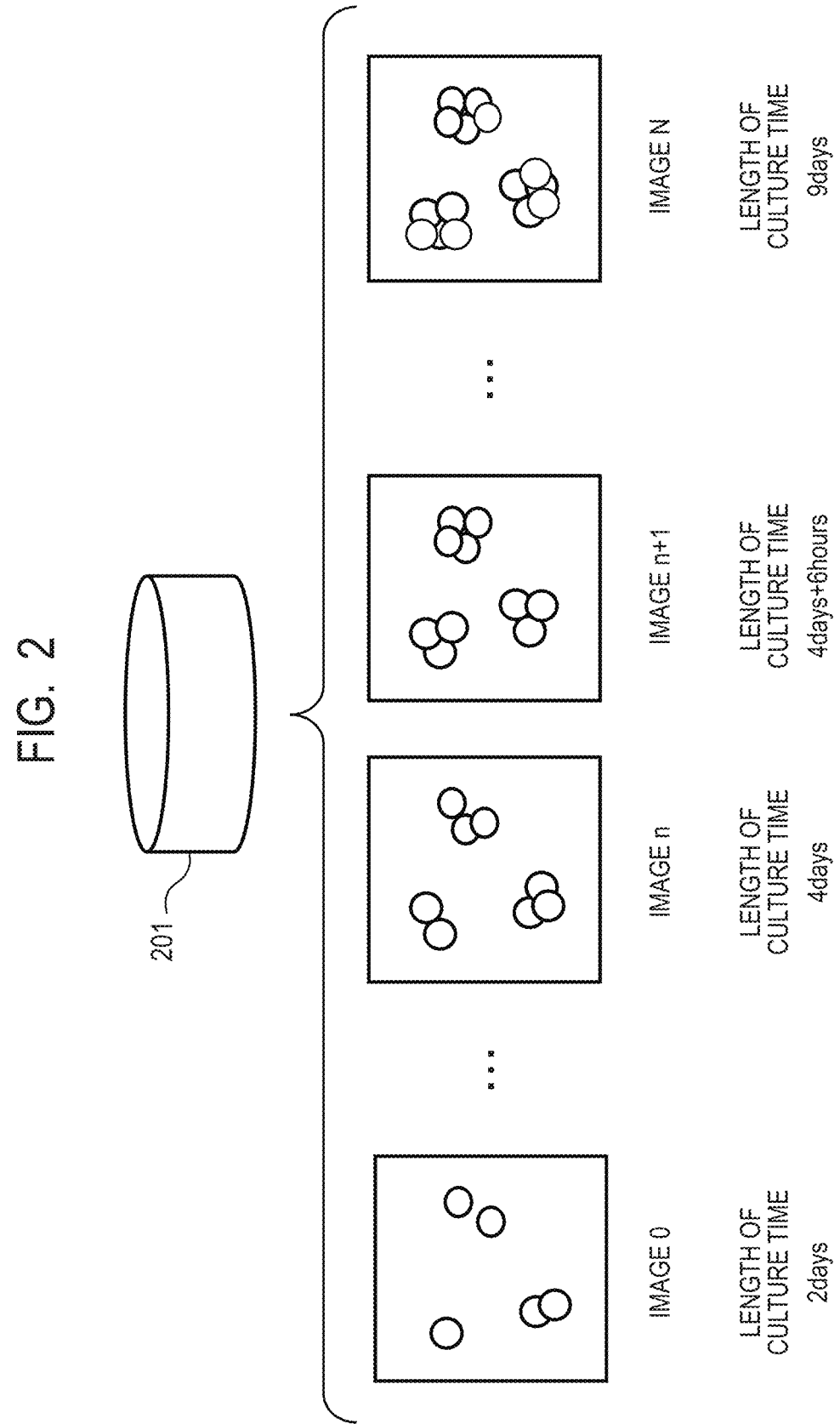
FIG. 2 is a diagram for illustrating an example of cell images acquired in Step S101 in the first embodiment.

An example of the cell image data acquired in Step S101 in culture of a stem cell in a culture vessel 201 is illustrated in FIG. 2. Cell images generated in time series are indexed in the order of image acquisition by symbols 0, 1, n, n+1, . . . , and N. A image acquisition date/time corresponding to each index symbol is also recorded so that the image acquisition date/time and the length of culture time of any image can be known.

Figure 3:
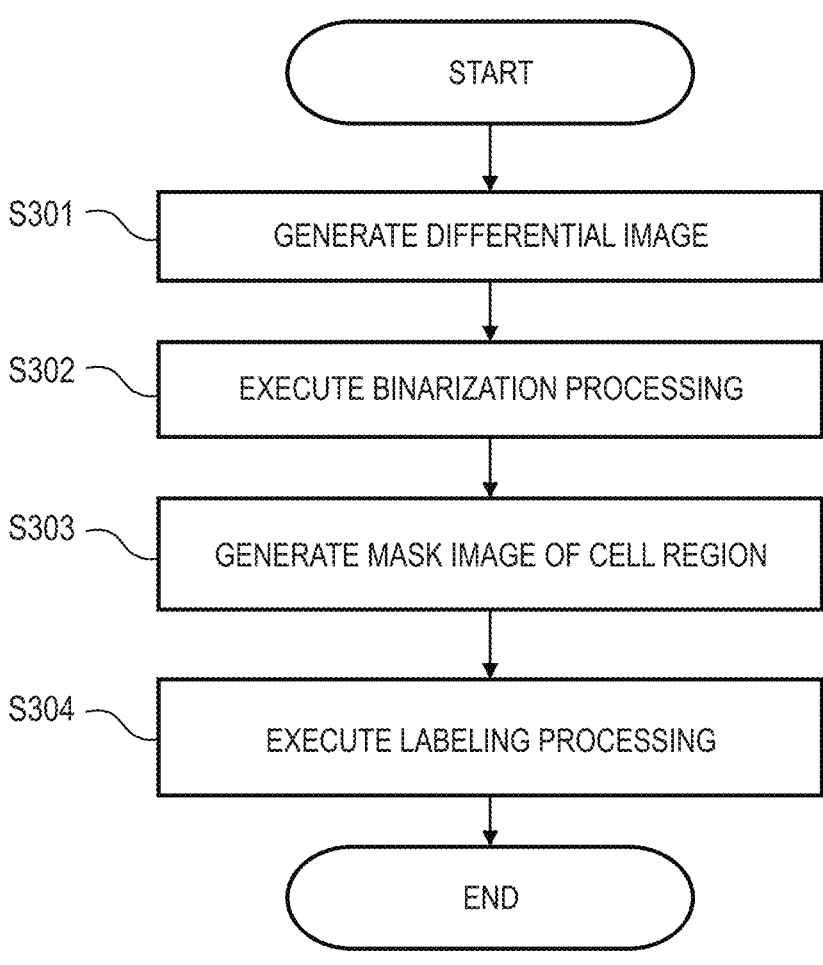
FIG. 3 is a flow chart for illustrating an example of a method of extracting cell regions in Step S102 in the first embodiment.

Step S102 is a cell region extraction step of extracting, from the cell image data acquired in Step S101, a plurality of cell regions where each cell region corresponds to one of a plurality of colonies. In Step S102, the cell regions are extracted from the cell image data acquired in Step S101. FIG. 3 is a flow chart for illustrating a flow of a processing step of Step S102. In the following description, a method of extracting cell regions is described with reference to FIG. 3.

In Step S301, a differential image is generated by applying a differential filter to one cell image. The differential image is obtained by calculating, for each pixel, an amount of change in luminance value between the pixel and surrounding pixels, and expressing calculated amounts of change as an image. In a case of a cell image, the differential image is an image that has high luminance values in outline portions of cell regions and outline portions of cells within the cell regions.

In Step S302, regions having high luminance values in the differential image are extracted by performing binarization processing on the differential image generated in Step S301. In the binarization processing, any threshold value is set, and a value of each pixel of the differential image is replaced with 1 when the value is equal to or more than the threshold value, and with 0 when the value is less than the threshold value.

How the binarization processing is executed is not limited to the method in which any threshold value is set. For example, a method of automatically determining a threshold value such as binarization by Otsu's method or Li's method may be used. In a case of setting any threshold value, the threshold value is set so as to suit image acquisition conditions of the apparatus such as the length of exposure to light and focus settings. A method of determining a threshold for each pixel of an image such as adaptive binarization may also be used. Through the binarization processing, a binary image expressed by setting 1 to pixel values in a region in which the luminance value changes greatly and 0 to pixel values in other regions (hereinafter referred to as "edge image") is created.

In Step S303, a mask image of cell regions is generated based on the edge image generated in Step S302. Here, the mask image is a binary image in which cell regions are expressed by a pixel value of 1 and other regions are expressed by a pixel value of 0. The mask image is generated by extracting regions to which a pixel value of 1 is linked in the edge image, and replacing the pixel values inside each linked region with 1.

In Step S304, a label image in which individual cell regions are discriminated from each other is generated by performing labeling processing on the mask image generated in Step S303. In the labeling processing, regions to which a pixel value of 1 is linked in the mask image are extracted, and, for each linked region, operation of replacing values of pixels in that region with pixel values different from one another is performed.

A threshold value for the size of a cell region may be set to exclude cell regions of sizes smaller than the threshold value. For example, an area of 10,000 $\mu m^2$ may be set as the threshold value in the case of a stem cell. In labeling of each linked component of the mask image, the area of the linked region is calculated, and the pixel value of that linked region is set to 0 when the area is equal to or less than the threshold value.

The processing steps of from Step S301 to Step S304 described above are executed for each of the images generated in time series, and cell regions in each of the images are thus acquired.

The cell region extraction processing based on the differential filter in Step S301 to Step S304 utilizes the fact that there is a difference in brightness/darkness at a boundary of a cell region in the image. Accordingly, this cell region extraction processing is favorably executable not only in an image acquired by phase contrast observation but also in an image in which an outline of a cell region is clear. For example, observation methods other than phase contrast observation, such as differential interference observation and modulation contrast observation, are given as a method of visualizing a phase object. A technology of visualizing a phase object even in bright field observation by devising an optimum apparatus configuration or optimum image processing is publicly known, and the present invention is applicable also to an image obtained by that technology.

An example of extracting cell regions from a cell image 401 is illustrated in FIG. 4. A mask image 402 is the image generated in Step S303, and uses a white color to indicate a background region and a black color to indicate cell regions. The labeling processing of Step S304 is performed on the mask image, with the result that isolated individual cell regions such as cell regions T01, T02, and T03 illustrated in FIG. 4 are discriminated from one another. The cell regions can thus be extracted.

In the extraction, in a case in which a target colony from which a cell region is to be extracted is in contact with at least one selected from outer circumferences of the culture vessel and of an image pickup field, it is preferred to exclude such a colony as a target from which a cell region is to be extracted. Whether a colony is in contact with the outer circumference of the culture vessel can be determined by setting an outline that indicates the culture vessel in advance, or extracting the outline of the culture vessel through Hough transform or a similar method, and determining whether a cell region corresponding to the target colony overlaps with the outline. Similarly, whether a colony is in contact with the outer circumference of the image pickup field can be determined by determining whether a cell region corresponding to the target colony overlaps with the outer circumference of the acquired image.

Step S102 may include exclusion of, in a case in which two or more colonies come into contact with one another in the process of culture and join together to form one colony, such a colony as a target from which a cell region is to be extracted.

That is, Step S102 may include determination about whether a colony in cell image data acquired at a time point A along the time series is formed by joining of two or more colonies in cell image data acquired at a time point B which precedes the time point A along the time series. When it is determined that the colony in the cell image data of the time point A is formed by joining of two or more colonies in the cell image data of the time point B, Step S102 may further include exclusion of the colony in the cell image data of the time point A that has been formed by the joining described above as a target from which a cell region is to be extracted.

Step S103 is a data calculation step of calculating, for each of the plurality of cell regions extracted in Step S102, data about the size of the cell region. Examples of numerical values that can be used as the size of a cell region include the area of the cell region, the length of a circumference of the cell region, a radius of the cell region, and a diameter of the cell region. In the following description, the area of a cell region is calculated as the size of the cell region.

With respect to any cell region extracted from a cell image of a specific image "n," which cell region of a next image n+1 corresponds to the identical colony with a colony of the extracted cell region can be determined with use of position information of cell regions. For example, in pieces of cell image data acquired at different time points in the time series, a cell region in one of the pieces of cell image data and a cell region in another of the pieces of cell image data that correspond to the identical colony can be determined based on at least one selected from centroids of cell regions and the degree of overlapping between the cell regions. The following description is about a method of determining which cell regions correspond to the identical colony in a plurality of images generated in time series based on processing of centroids of cell regions.

Figure 5:
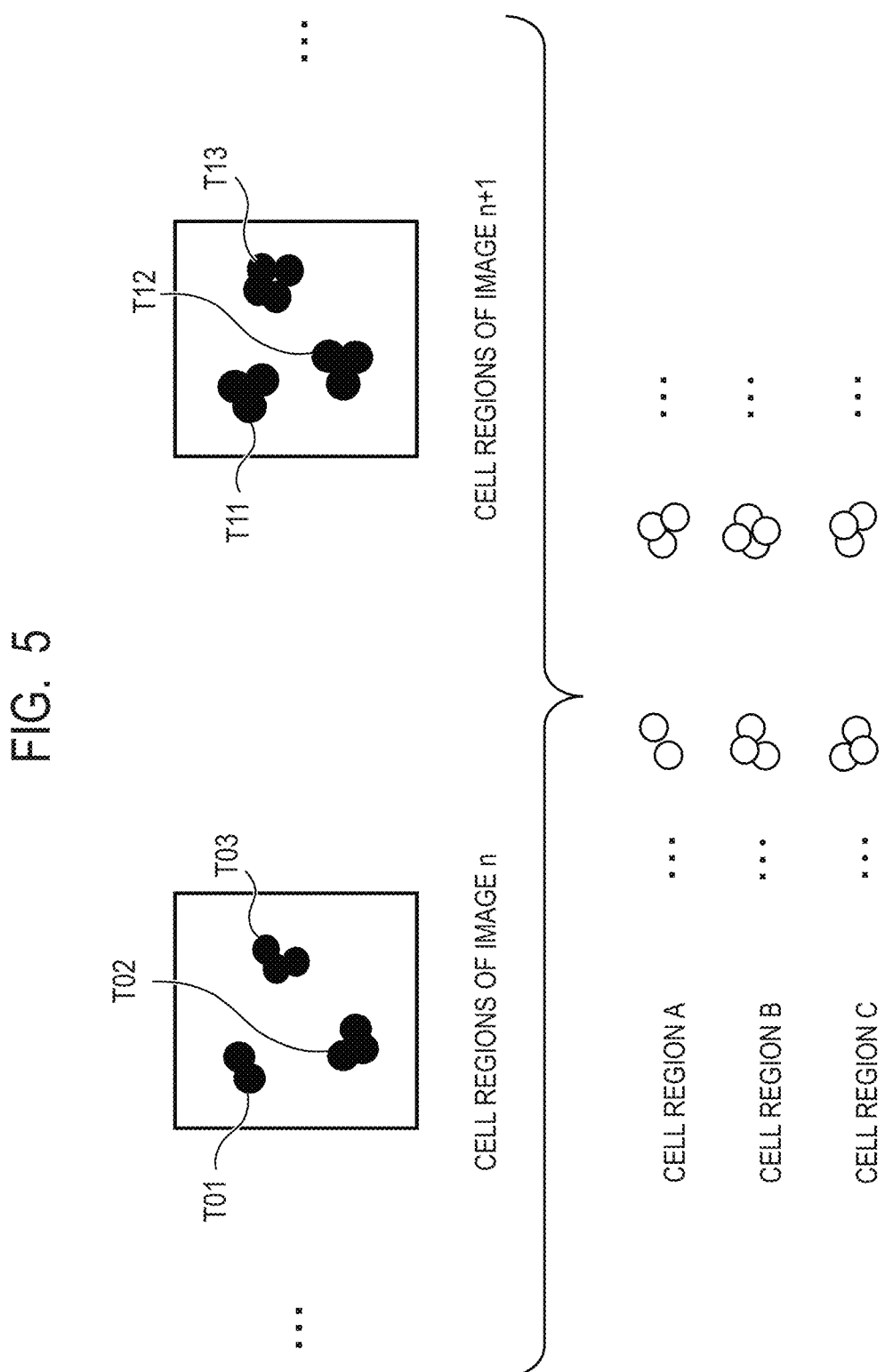
FIG. 5 is a diagram for illustrating an example of the cell regions extracted from a plurality of cell images in Step S102 in the first embodiment.

FIG. 5 is a diagram for illustrating an example of the cell regions extracted from the cell images in Step S102. In the image "n," the cell regions T01 to T03 are extracted, and cell regions T11 to T13 are extracted in the image n+1.

First, distances of centroids of the cell regions T11 to T13 in the image n+1 from a centroid of the cell region T01 of the image "n" are calculated. The cell region having the centroid at the closest distance out of the calculated distances is then determined to be a cell region corresponding to the cell region T01. In the example of FIG. 5, the cell regions T01 and T11 are determined to be the same region.

Execution of the processing described above is repeated for each of the cell regions T02 and T03, to thereby determine, for any cell region extracted from the specific image "n," which cell region of the next image n+1 is the same cell region as the extracted cell region. A threshold value for the distance of the centroid may be set so that a cell region located at a certain distance or farther is determined to be not a corresponding cell region.

Subsequently, for a cell region of the image n+1, which cell region in a next image n+2 is the same cell region is determined. In this manner, the same processing is executed for every image along the time series, and time-series data about the size of a cell region of each colony can thus be acquired.

Figure 13:
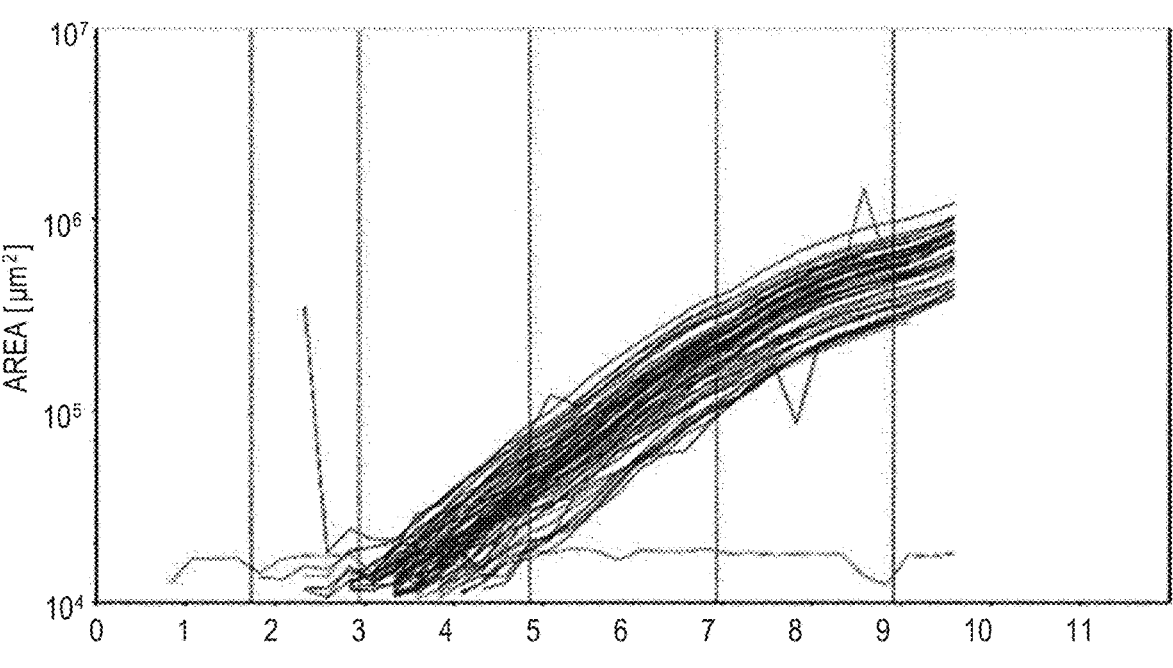
FIG. 13 is a graph for showing results of calculating the data of the size of each cell region in Step S103 in the first embodiment.

An example of changes in area calculated for each cell region in Step S103 is shown in FIG. 13. In a graph shown in FIG. 13, the axis of abscissa indicates the length of culture time and the axis of ordinate indicates the areas of cell regions. One line represents data about a cell region of one colony.

Figure 6:
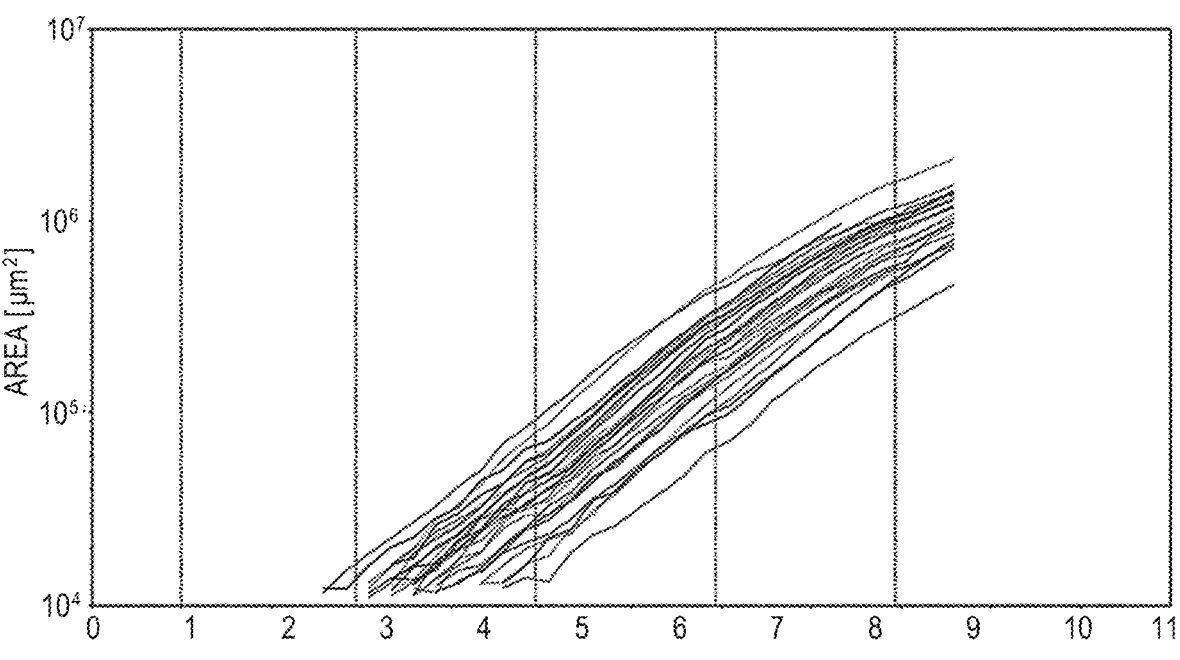
FIG. 6 is a graph for showing results of excluding abnormal values from data of a size of each cell region which is shown in FIG. 13.

A value that is not an accurate measurement result of the area (hereinafter referred to as "abnormal value") due to adhesion of, for example, dead cells, bubbles, and specks may be mixed in the time-series data of the colony area. Data indicating unsmooth changes in area in FIG. 13 is data including an abnormal value defined as above. Such data may be excluded by calculating fluctuations in change with time of the area. Specifically, Step S103 may include the following processing. With respect to data about cell region sizes calculated for cell regions corresponding to the identical colony, whether a value acquired at one certain time point in the time series has an amount of change equal to or more than a fixed value from a reference value, which is based on a value acquired at at least one other time point, is determined. When the value acquired at the one point has an amount of change equal to or more than the fixed value from the reference value, the data about cell region sizes calculated for cell regions corresponding to the identical colony is excluded. For example, a CV value of an amount of change in area may be calculated for each colony as the reference value so that a value having a CV value equal to or more than a threshold value is excluded from the data. The threshold value is set to, for example, 1.5, and may be set by a user to a value of the user's discretion. Results of excluding abnormal values from the data shown in FIG. 13, with the threshold value set to 1.5 are shown in FIG. 6.

Step S104 is a change point detection step of detecting a change point, which is timing of a change in state of a colony, based on the cell region sizes calculated in Step S103. In Step S104, the change point of a cell region is detected with use of the data acquired in Step S103 about the size of the cell region. The change point is detectable as a point at which a local maximum value of an approximate curve obtained as follows is given. First, a relationship between the time, or the cell region size, and a rate of change in cell region size is approximated as a polynomial model. A local maximum point in the obtained polynomial model is then obtained, and the obtained local maximum point can thus be detected as the change point. An example in which the change point is detected as a point at which a local maximum value of an approximate curve obtained by polynomial approximation of a relationship between the cell region size and the rate of change in cell region size is given is described.

First, time-series data about the rate of change in cell region size is acquired. A change rate Dn in the image "n" can be calculated by Expression (1). In Expression (1), Sn and to represent the size and the length of culture time, respectively, of a cell region in the image "n."

$$D_n = \frac{\log_2 S_{n+1} - \log_2 S_n}{t_{n+1} - t_n} \tag{1}$$

The time-series data about the rate of change in cell region size can be acquired by calculating the rate of change for cell regions of the identical colony in each of images generated in time series. Here, the rate of change in cell region size in the image "n" may be calculated with use of data of a fixed length of period. For example, data of past 2 days from the image "n" may be used to calculate the rate of change. In this case, a slope of a straight line obtained by linear approximation of a relationship between the length of culture time and the cell region size indicates the rate of change.

Subsequently, a change point of the colony is detected based on time-series data about the rate of change. The change point can be obtained by performing polynomial approximation of a relationship between the time-series data about the cell region size and time-series data about the rate of change, and detecting a local maximum value of a resultant approximate curve.

First, the relationship between the two pieces of data is approximated as a cubic polynomial model expressed by the following expression, with the rate of change given as "y" and the region size given as "x." In the expression, "a," "b," "c," and "d" represent parameters of a cubic polynomial calculated by the approximation.

$$y=ax^3+bx^2+cx+d \tag{2}$$

A local maximum point of a cubic curve obtained by the approximation is then obtained, to thereby detect the change point. Here, data about the cell region size, the rate of change, or the length of culture time that is associated with a change point is referred to as "change point data."

The operation described above is performed on data about cell regions of each colony, to thereby detect the change point of each colony, and the change point data of each change point can be obtained.

Figure 7:
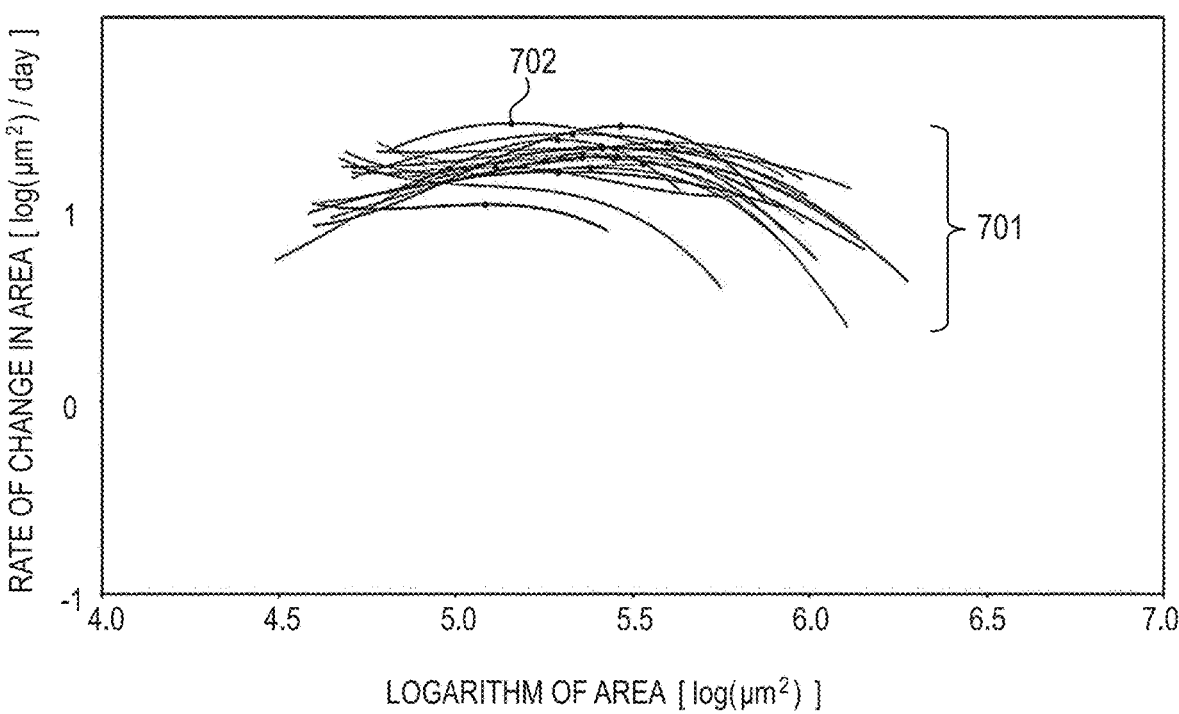
FIG. 7 is a graph for showing an example of results of detecting a change point in Step S104 in the first embodiment.

FIG. 7 shows results of an approximate curve 701 obtained for each colony and a detected local maximum point 702. The axis of abscissa indicates the areas of cell regions, the axis of ordinate indicates the rate of change, and the approximate curve 701 of each colony and the detected local maximum point 702 are shown. A graph in which the change point of each colony is output in this manner enables a worker to accurately grasp change points of colonies.

How the change point data is output to the worker is not limited to the method of outputting in the form of a graph such as the one illustrated in FIG. 7. For example, the change point data may be output in a list format. In the output change point data, the numerical value of the area of a cell region may be converted into another index such as the radius or the length of the circumference. Results output in a list format in which the area of a cell region at the change point is converted into the radius are shown in FIG. 8.

The change point obtained in this manner varies depending on differences in culture conditions such as a cell line of the stem cell, an amount of culture medium, and a seeding density. The change point also varies from colony to colony out of a plurality of colonies present in the culture vessel.

Here, that the cell line of a cell differs means that a raw material cell originates from a different donor or a different tissue.

An example in which a distribution of change point data varies depending on differences in culture condition is described below with reference to FIG. 14 to FIG. 19. In the example described below, data obtained by converting an area that corresponds to the change point of each colony into a diameter and the rate of change in area are used as the change point data.

Figure 14:
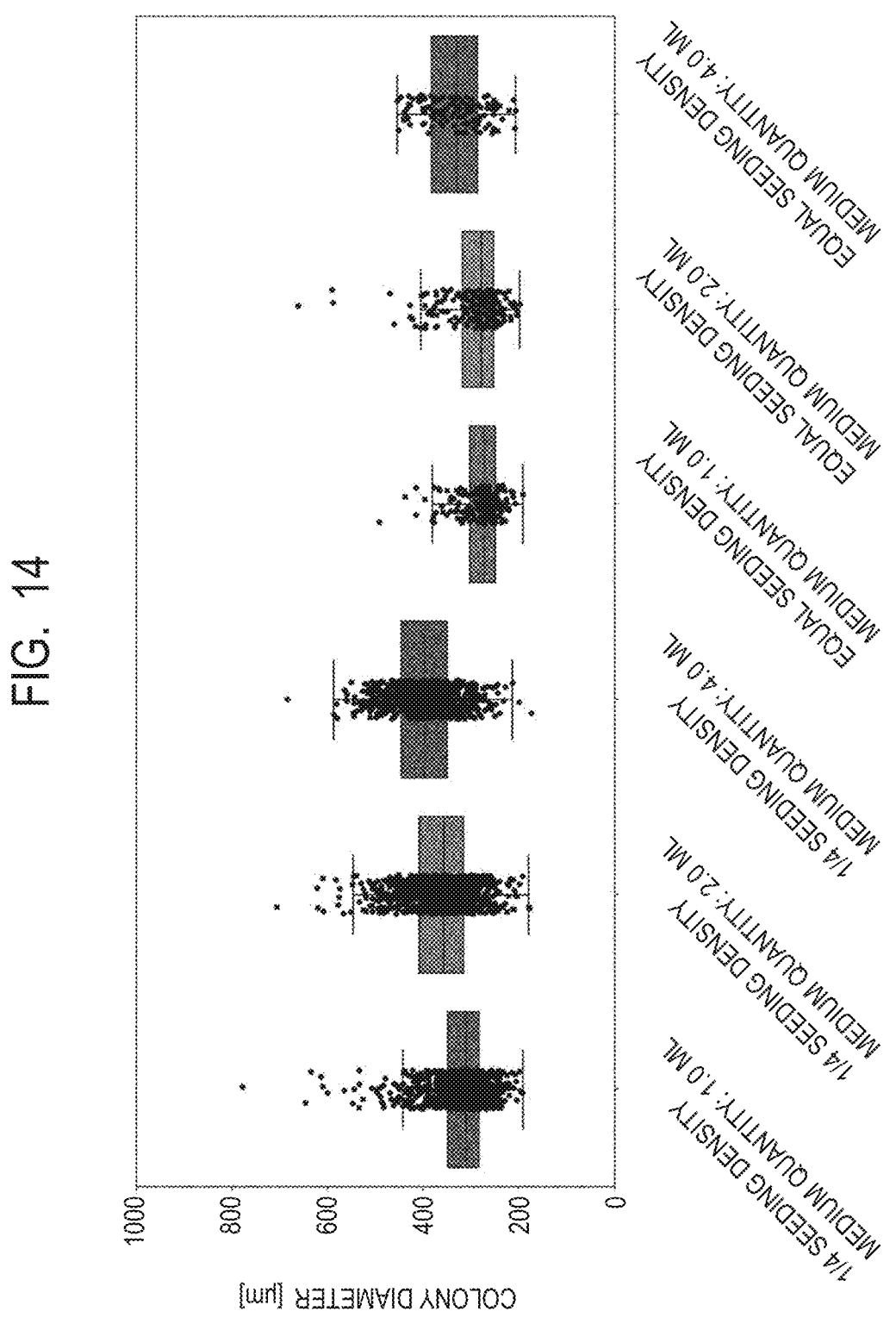
Figure 15:
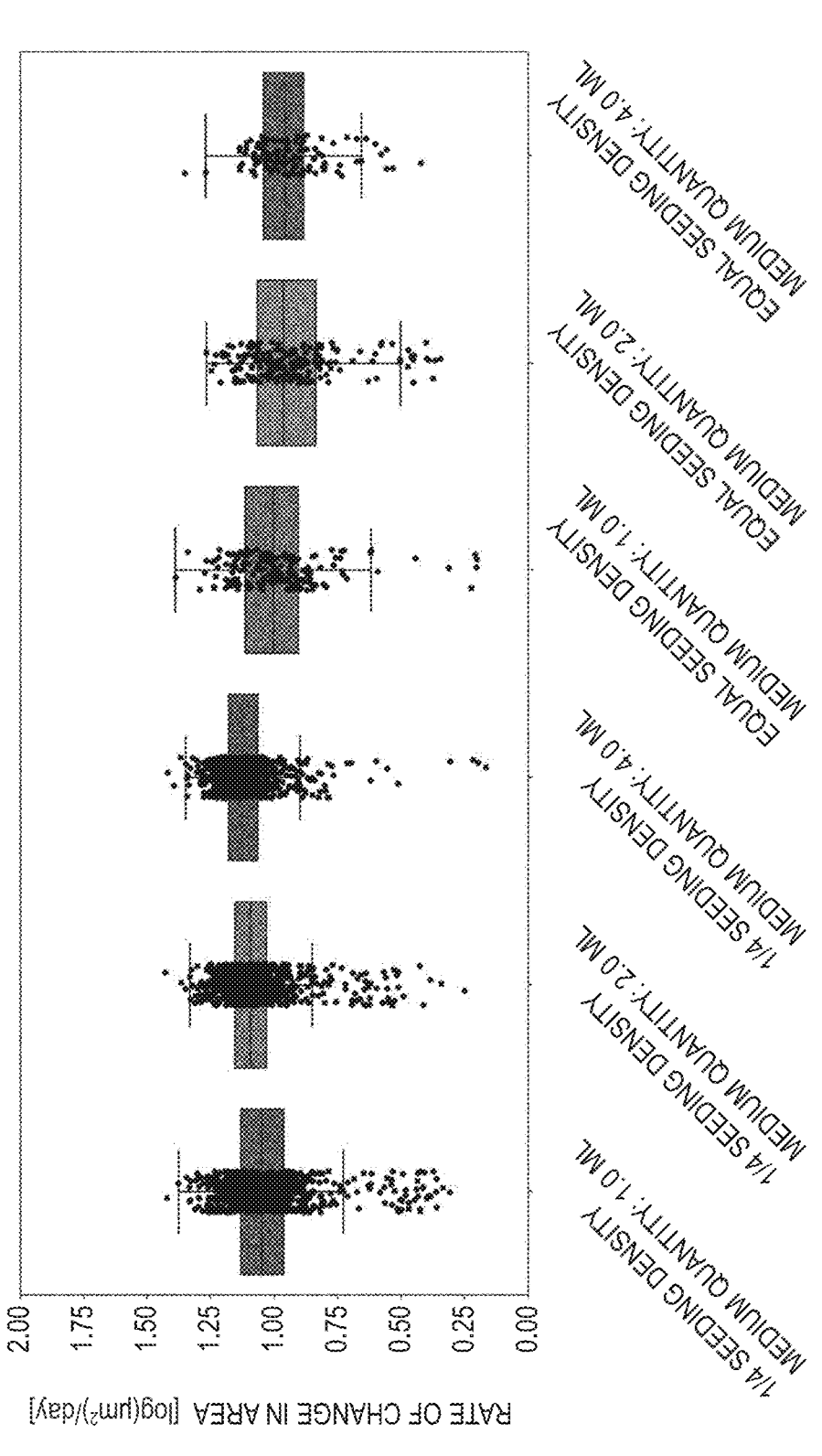
FIG. 15 is a graph for showing results of comparing distributions of rates at which the area changes at change points depending on the seeding density and on the medium quantity.

FIG. 14 and FIG. 15 are each a graph for showing an example of variations in distribution of change points depending on changes in seeding density and in medium quantity. Here, an iPS cell was cultured in a general 6-well plate, with the seeding density varied, or the amount of every two days medium replacement varied, and a distribution of the change point data in each culture is shown in a box plot. The iPS cell was cultured with the seeding density varied at an equal density (13,000 cells/well) and at a quarter density (3,250 cells/well), and the amount of every two days medium replacement varied at 1.0 ml/well, 2.0 ml/well, and 4.0 ml/well.

Of the change point data, the colony diameter is used in FIG. 14, in which distributions of colony diameters are shown, and the rate of change in area is used in FIG. 15, in which distributions of rates of change in area are shown. It is understood from FIG. 14 that the colony diameter at the change point tends to be large when the medium quantity is larger or when the seeding density is lower.

Figure 16:
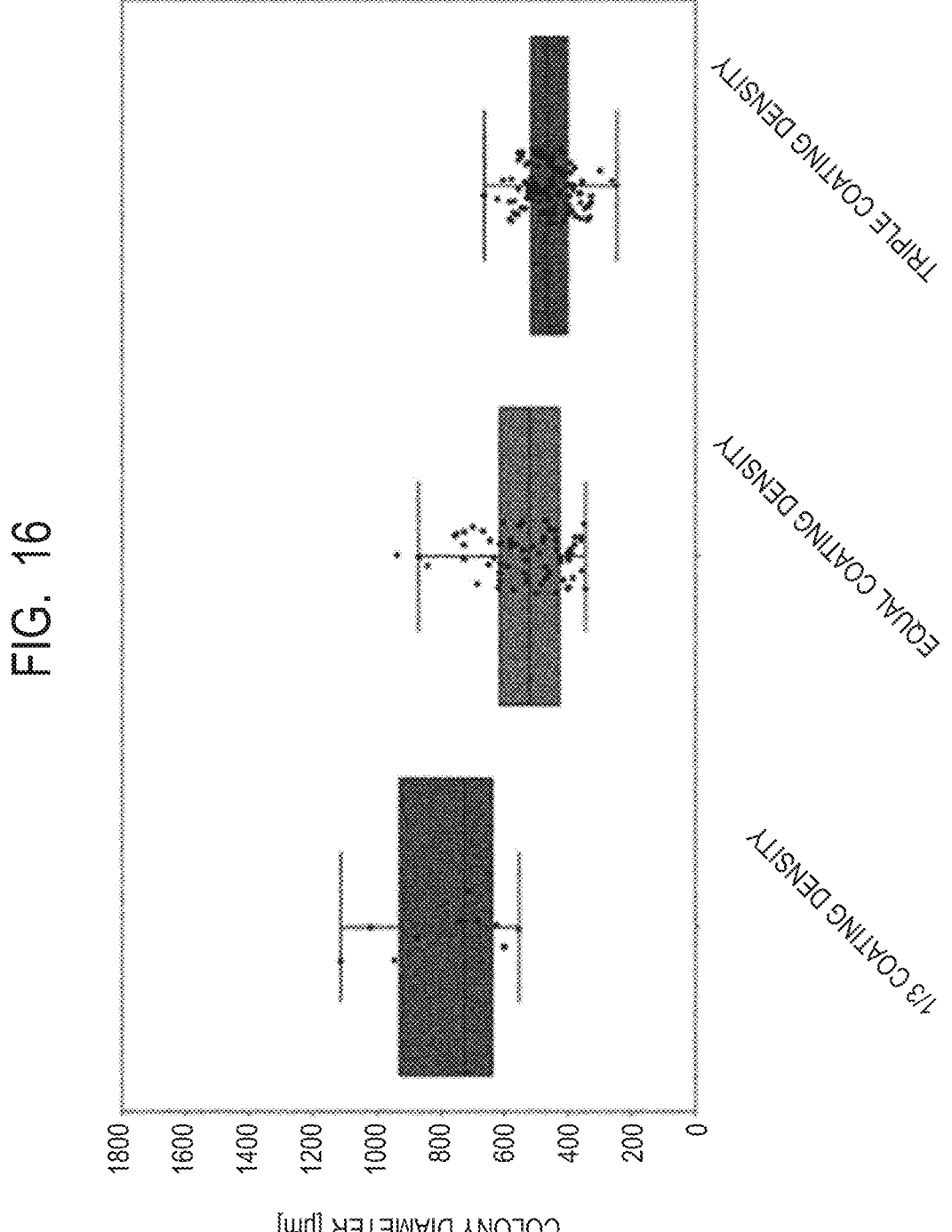
FIG. 16 is a graph for showing results of comparing distributions of colony diameters at change points depending on a coating density.
Figure 17:
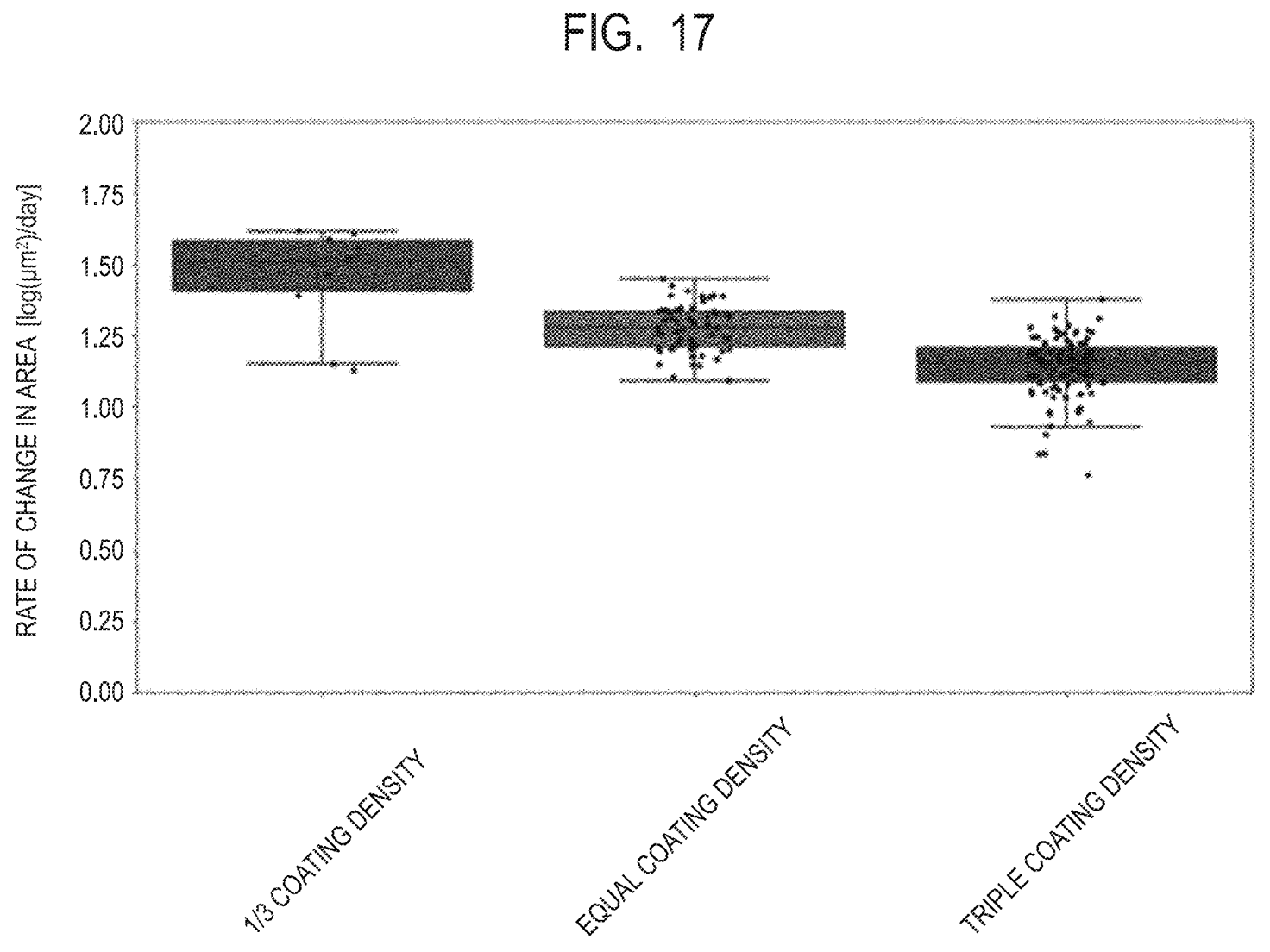

FIG. 16 and FIG. 17 are each a graph for showing an example of variations in distribution of change points depending on changes in coating density. The coating density is the amount of a solution for surface treatment performed on the culture vessel in advance for adherent cell culture. Here, an iPS cell was cultured in a general 12-well plate by varying the amount of an iMatrix coat, and a distribution of the change point data in each culture is shown in a box plot. The iPS cell was cultured with the iMatrix coating density varied at a one-third amount (0.63 μg/well), an equal amount (1.9 μg/well), and a triple amount (5.7 μg/well).

Of the change point data, the colony diameter is used in FIG. 16, in which distributions of colony diameters are shown, and the rate of change in area is used in FIG. 17, in which distributions of rates of change in area are shown. It is understood from FIG. 16 that the colony diameter at the change point tends to be large when the coating density is smaller. It is also understood from FIG. 17 that the coating density affects the rate of change in area as well, and that the rate of change is lower when the coating density is larger.

Figure 18:
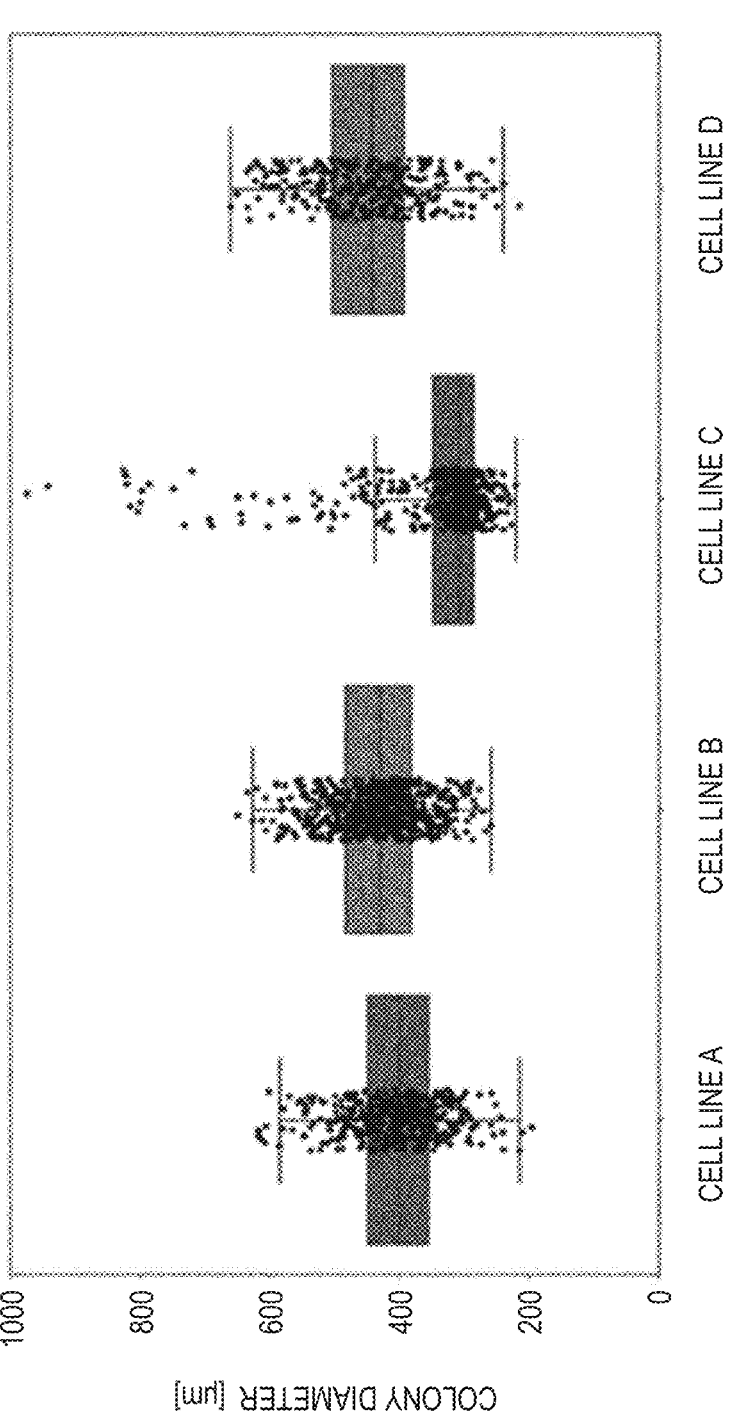
FIG. 18 is a graph for showing results of comparing distributions of colony diameters at change points depending on a cell line.
Figure 19:
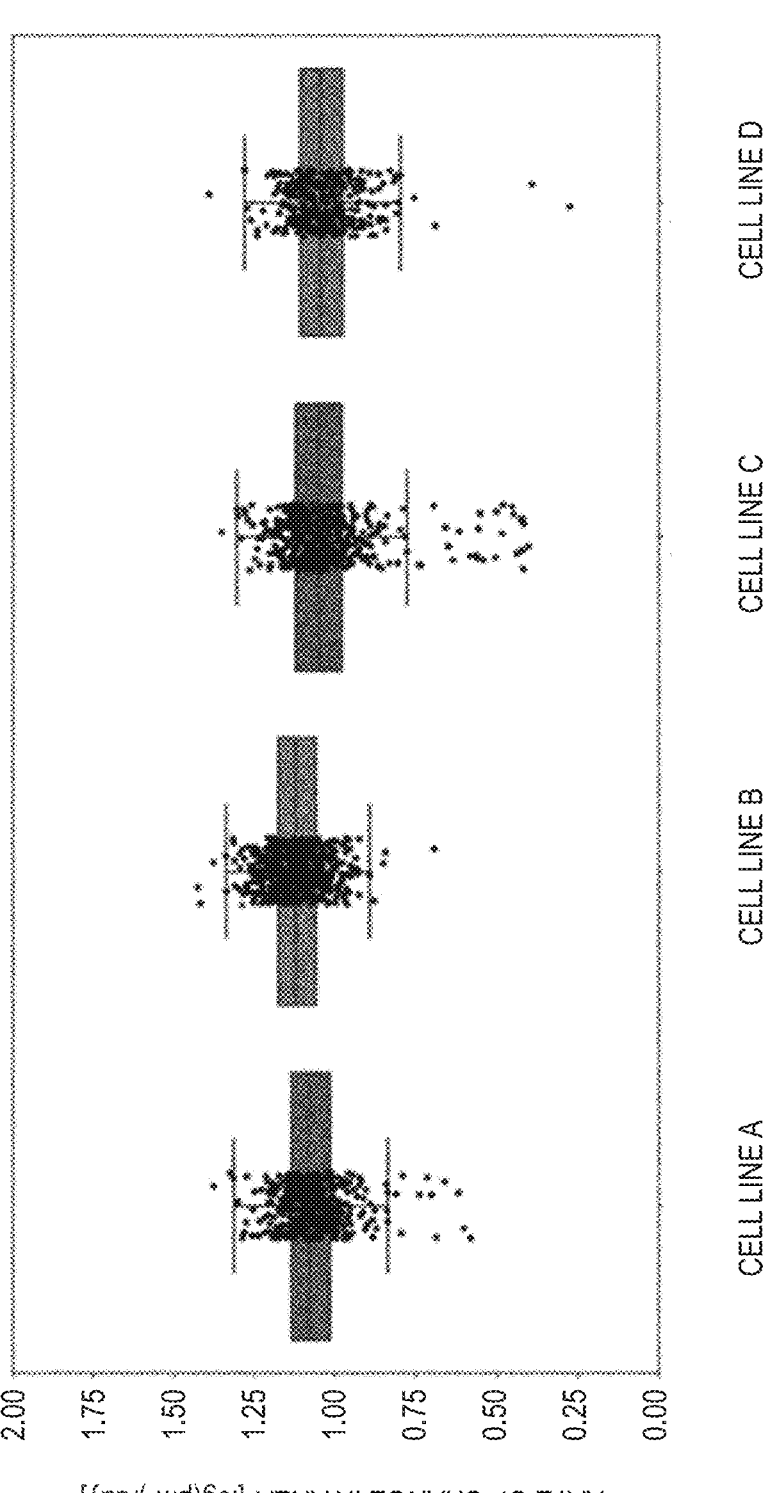
FIG. 19 is a graph for showing results of comparing distributions of rates at which the area changes at change points depending on the cell line.

FIG. 18 and FIG. 19 are each a graph for showing an example of variations in distribution of change points depending on differences in cell line of a stem cell. Cell lines A, B, C, and D, four types in total, were cultured, and a distribution of change point data in each culture is shown in a box plot in FIG. 18 and FIG. 19.

Of the change point data, the colony diameter is used in FIG. 18, in which distributions of colony diameters are shown, and the rate of change in area is used in FIG. 19, in which distributions of rates of change in area are shown.

As shown in FIG. 18, Cell line C tends to be small in terms of colony diameter at the change point, compared to the other three types of cell lines. This suggests a possibility that Cell line C is a cell line having a feature different from a feature of the other three types.

This concludes the description given with reference to FIG. 14 to FIG. 19 on the example in which the change point data calculated according to the first embodiment is applied to data varied in culture conditions to compare the data.

In order to improve reproducibility and stability of cell culture, the worker can make use of the change point grasped in the first embodiment in determining timing of cell processing.

According to the first embodiment described above, the change point of a colony is caught from cell image data, and the worker can accurately grasp timing at which an efficiency of colony growth decreases.

Modification Example 1 of First Embodiment

In Step S102, how to extract a cell region is described but is not limited to the method that uses a differential filter. For example, a correct image of a cell region may be prepared to execute cell region extraction by machine learning.

Modification Example 2 of First Embodiment

In the description given above on Step S102, cell regions are extracted in a plurality of images generated in time series, and cell regions of the identical colony are identified with use of position information. In a case in which position misalignment is caused between the image "n" and the image n+1 by movement of a cell region, shifting of the culture vessel or scanning position in the observation apparatus, or the like, positioning of the image "n" and the image n+1 may be executed prior to the processing step of Step S102. For the positioning of two images, template matching, a phase-only correlation method, or a similar method can be used.

Modification Example 3 of First Embodiment

In the description given above on Step S103, cell regions are extracted in a plurality of images generated in time series, and cell regions of the identical colony are identified with use of the distance between centroids. In Modification Example 3 of the first embodiment, a method of identifying cell regions of the identical colony by calculating the degree of overlapping between cell regions is described.

Specifically, an overlapping degree "m" of two cell regions, for example, T01 and T11 illustrated in FIG. 5, is calculated by Expression 3.

$$m = \frac{S(T_{01} \cap T_{11})}{\mathrm{MIN}(S(T_{01}), S(T_{11}))} \tag{3}$$

In Expression (3), S represents the area of a region. For example, S(T01) represents the area of the cell region T01. T01∩T11 represents a region in which the cell region T01 and the cell region T11 overlap with each other.

The overlapping degree "m" takes a numerical value that is larger when the cell region T11 overlaps with the cell region T01 to a greater degree. The overlapping degree "m" of the cell region T12 and the overlapping degree "m" of the cell region T13 with respect to the cell region T01 are calculated as well, and the cell region that has the largest numerical value as the overlapping degree "m" can be determined to be a cell region corresponding to the cell region T01.

Modification Example 4 of First Embodiment

In the description given above on Step S102, cell regions are extracted in a plurality of images generated in time series, and cell regions of the identical colony are identified with use of position information. There is a case in which some of a plurality of cell regions extracted in the image "n" are joined together in the image n+1. In that case, the cell region created by joining of cell regions may be excluded from extraction results at that point.

Modification Example 5 of First Embodiment

In Modification Example 4 of the first embodiment, the method of excluding a cell region that has been created by joining of cell regions is described. The region created by joining of regions, however, may be divided into a plurality of cell regions by region division. In that case, the region that is joined regions can be divided by applying a level set method, a watershed method, the GrabCut method, or a similar method to the region that is joined regions.

Modification Example 6 of First Embodiment

In Step S104, the method of detecting the change point by performing polynomial approximation on a relationship between the cell region size and the rate of change in cell region size, and obtaining a local maximum point is described. The mode of carrying out the present invention is not limited thereto, and the change point may be detected by performing polynomial approximation on a relationship between the length of culture time and the rate of change in cell region size, and obtaining a local maximum point. In that case, the change point can be detected by performing approximation to a cubic polynomial model expressed by Expression (2), with the rate of change given as "y" and the region size given as "x," and detecting a local maximum point of a resultant approximate curve.

Second Embodiment

In the first embodiment, the method of detecting the change point of a colony with use of cell image data generated in time series is described. This change point varies depending on a fine difference in culture condition, and the evaluation value is accordingly usable for determination of whether a cell has been cultured in a manner expected by a worker. In a second embodiment, a method of calculating an evaluation value for a certain culture condition of cell culture based on a detected change point of the cell culture under the culture condition is described.

Figure 9:
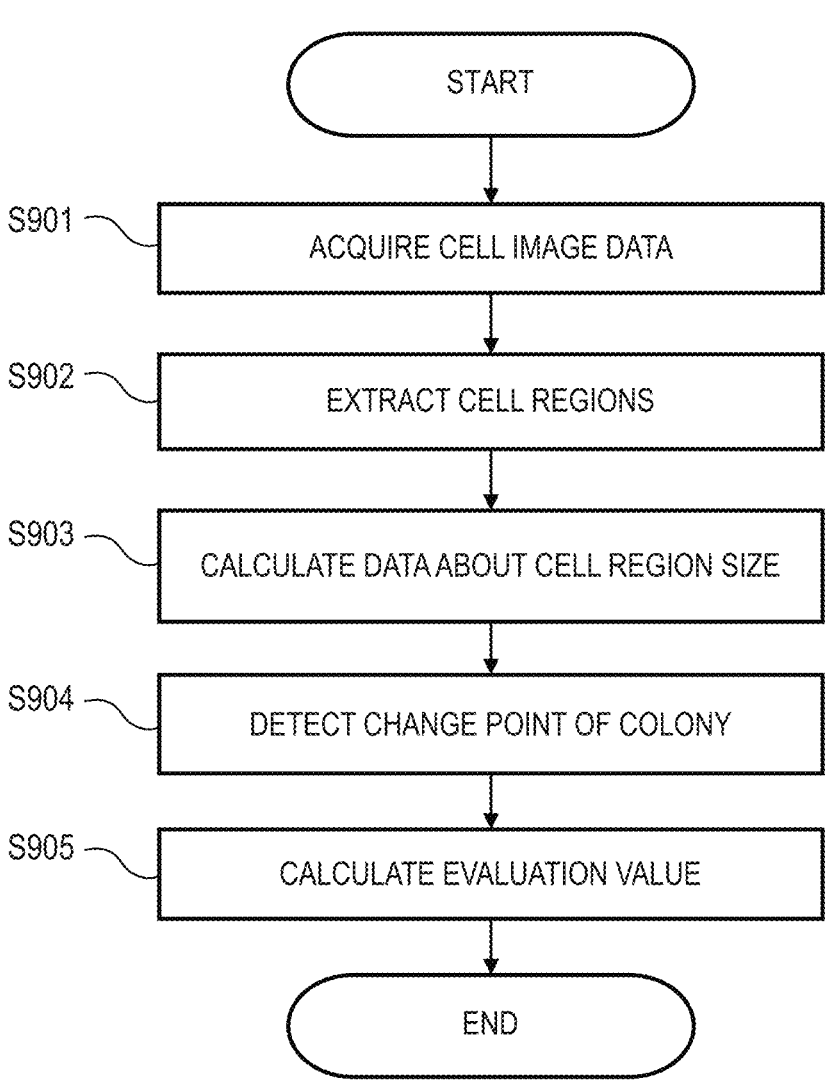
FIG. 9 is a flow chart of a cell image analysis method according to a second embodiment.

FIG. 9 is a flow chart of a cell image analysis method according to the second embodiment.

Step S901, Step S902, Step S903, and Step S904 are the same as Step S101, Step S102, Step S103, and Step S104 of FIG. 1, respectively, and descriptions thereof are accordingly omitted.

Step S905 is an evaluation value calculation step of calculating an evaluation value for a culture condition adopted in cell culture, based on the change point. In Step S905, the evaluation value is calculated based on the change point data calculated for colonies in Step S904. The evaluation value here is a value indicating an evaluation of a culture state in cell culture under an adopted culture condition.

For example, a proportion of colonies for which change points have been detected to colonies of the cell regions detected in Step S902 is calculated. A threshold value may be set for the rate of change in cell region size out of the change point data to obtain the proportion of cell regions that have rates of change in cell region size equal to or less than the threshold value. This enables evaluation about the proportion of colonies starting to decrease in growth efficiency in cell culture.

The evaluation value calculation step may include calculation of at least one type selected from average value, standard deviation, CV value, median value, and other statistics with respect to the change point data. The change point data here is at least one type of data selected from time, cell region size, and rate of change in cell region size that corresponds to a change point in each of a plurality of colonies.

For example, the evaluation value may be calculated by calculating a CV value (variation coefficient) from data about the cell region size out of the change point data of each colony. Here, the CV value may be calculated from data of the rate of change in size, or an average of the CV value calculated from data about the cell region size and the CV value calculated from data of the rate of change in size may be obtained. This enables evaluation about whether cells being cultured are cultured in a uniform manner.

A plurality of statistics may be calculated as the evaluation value. Results of calculating statistics with respect to the colony diameter data shown in FIG. 14, which is data about colony diameters at change points in six types of culture varied in seeding density and medium quantity, are shown in FIG. 20. The worker can determine whether cells have been cultured in an expected manner by referring to table information about statistics of change point data calculated for varied culture conditions in advance as in FIG. 20. For example, comparison of median values of FIG. 20 reveals that, when the seeding density is low or the medium quantity is large, the colony diameters at the change points are large, which suggests that whether cells in the vessel are nourished well is successfully evaluated. The worker can use those results for a quantitative check of the state of a cell being cultured, and for feedback with regards to a culture condition for the next time. The evaluation value may vary depending on the cell line, and is accordingly usable for a cell characteristics test as well.

Figure 21:
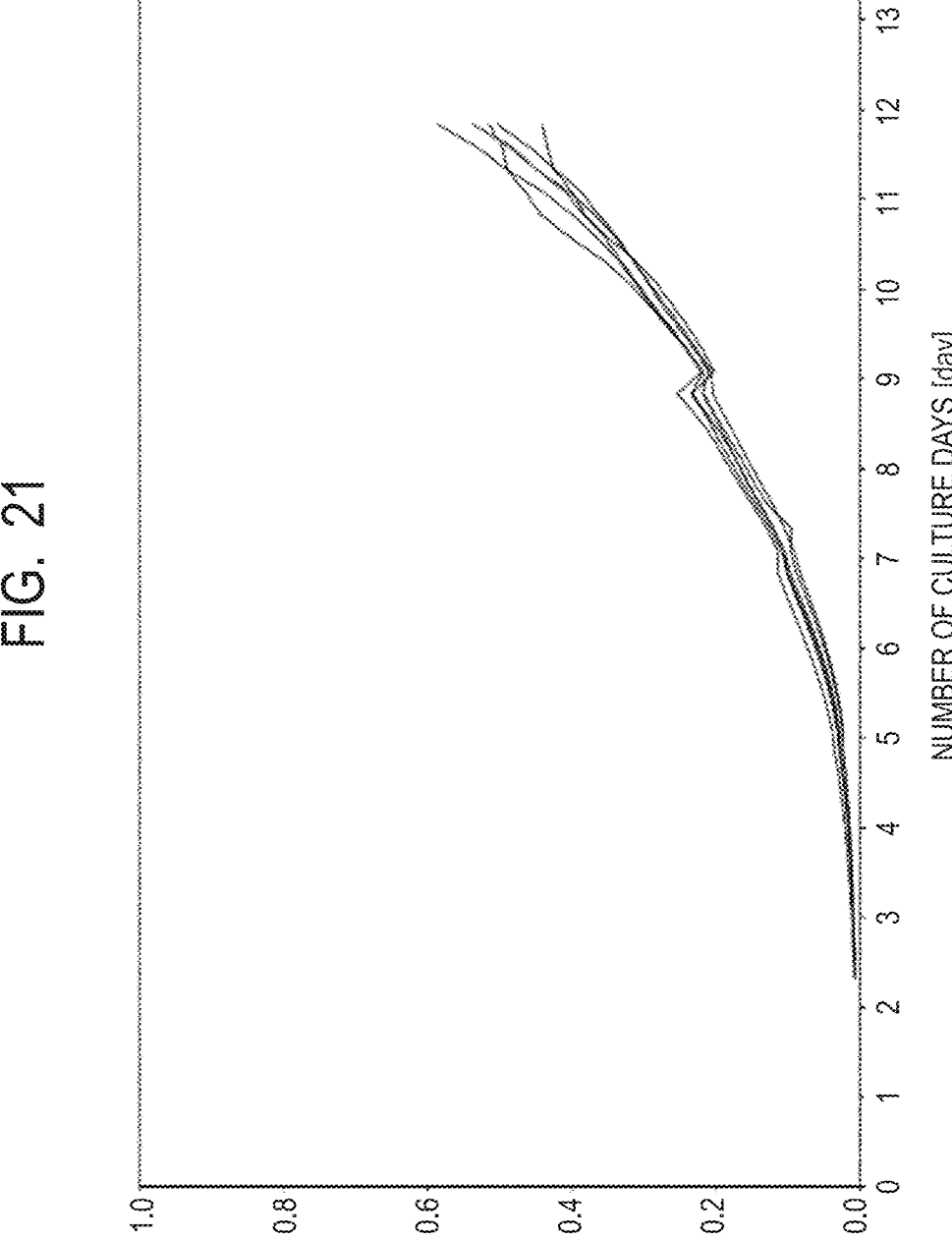
FIG. 21 is a graph for showing changes of confluences in culture vessels placed under different culture conditions.
Figure 22:
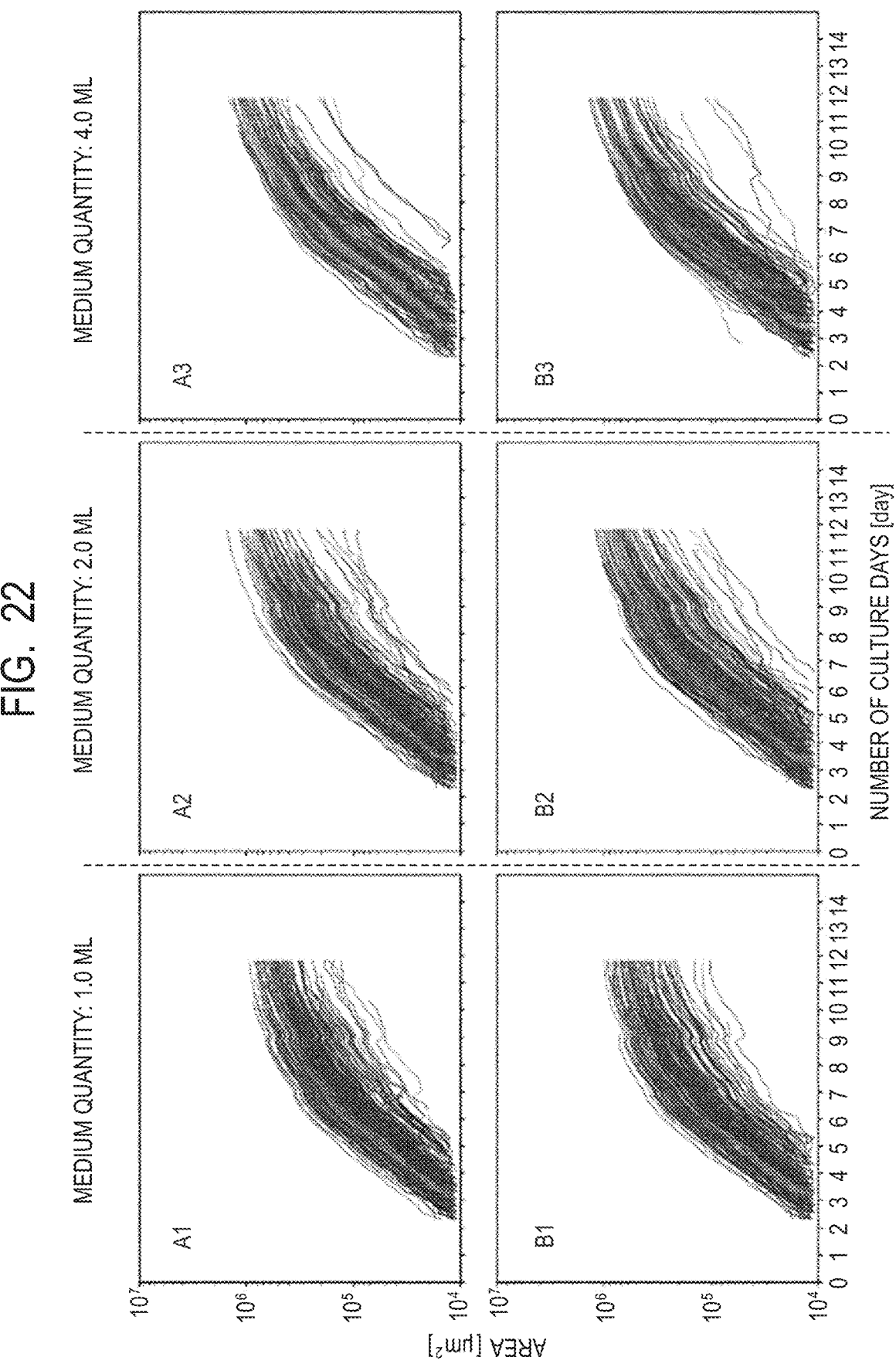
FIG. 22 is a group of graphs for showing changes of colony areas in culture vessels placed under culture conditions.

Acquisition of the evaluation value enables quantitative comparison of differences in culture condition or between cell lines, unlike the related art in which a confluence (the area of a part of a culture vessel that is taken up by a cell region) is monitored, or a growth behavior of a colony is simply compared. An example of results of comparison in confluence and in growth behavior of a colony between culture vessels varying in culture condition is shown in FIG. 21 and FIG. 22. FIG. 21 and FIG. 22 are graphs for showing measurement results of six culture vessels, namely, A1 to A3 and B1 to B3. A1 and B1, A2 and B2, and A3 and B3 are each a pair of vessels that share the same condition in terms of medium quantity with each other. It is understood from FIG. 21 and FIG. 22 that, with the methods of the related art, comparison of changes in colony growth behavior due to changes in medium quantity is difficult, and that calculation of the evaluation value as shown in FIG. 20 enables quantitative comparison of colony growth behavior.

This concludes the description about the method in which an evaluation value is calculated for a certain culture condition of cell culture, based on a detected change point of the cell culture under the culture condition. The evaluation value can be calculated by several methods as described above, and an evaluation value calculated by all of the described calculation methods may be output. Alternatively, the worker may select a method to be used to calculate the evaluation value.

As described above, according to the second embodiment, a culture state is evaluated based on the change point data, and the evaluation is usable to determine whether a cell has been cultured in a manner expected by the worker.

Third Embodiment

In the second embodiment, the method in which an evaluation value is calculated for a culture condition of cell culture based on a detected change point is described. The change point varies depending on a fine difference in culture condition, and the evaluation value is accordingly usable by a worker to compare states of a plurality of cell cultures with one another when a different culture condition is used for each of the plurality of cell cultures. In a third embodiment, a method of calculating an evaluation value when cell image data generated in time series includes data of a plurality of cell cultures cultured under conditions different from one another is described.

FIG. 10 is a flow chart of a cell image analysis method according to the third embodiment.

In the cell image analysis method according to the third embodiment, the evaluation value calculation step described above includes calculation of a first evaluation value for each of the plurality of cell cultures, and calculation of a second evaluation value calculated with respect to culture conditions different from another, based on the first evaluation value.

Specifically, in Step S1001, cell image data generated in time series about cell cultures cultured under a plurality of conditions is acquired. Here, the cell image data to be acquired is divided into evaluation target data and reference data.

A period and a time interval of the cell image data to be acquired are set by the same method as the method of Step S101 in the first embodiment. The worker can select which culture condition is a culture condition of a cell culture for acquiring data to be used as evaluation target data, and which culture condition is a culture condition of a cell culture for acquiring data to be used as reference data. In the following description, it is assumed that cell image data about an (i+1)th passage culture in a process of culturing a stem cell maintaining an undifferentiated state is selected as evaluation target data, and that cell image data about an i-th passage culture is selected as reference data.

In Step S1002, change point data is acquired for each piece of cell image data acquired in Step S1001. The change point data is acquired by the same method as the method in Step S101, Step S102, Step S103, and Step S104 in the first embodiment. The change point data corresponding to the evaluation target data and the change point data corresponding to the reference data can thus be acquired.

In Step S1003, the first evaluation value in cell culture is calculated based on the change point data acquired for each cell culture in Step S1002. The first evaluation value is calculated by the same method as the method of Step S905 in the second embodiment. The first evaluation value corresponding to the evaluation target data and the first evaluation value corresponding to the reference data can thus be calculated.

In Step S1004, the second evaluation value is calculated based on the first evaluation values calculated in Step S1003. In a case in which a first evaluation value $E_o$ is calculated for the evaluation target data and a first evaluation value $E_r$ is calculated for the reference data in Step S1003, a second evaluation value E can be calculated by Expression 4.

$$E = E_o - E_r \qquad (4)$$

As described above, according to the third embodiment, the second evaluation value can be calculated when cell image data generated in time series includes data about a plurality of cell cultures cultured under conditions different from one another.

The third embodiment is effective for a check performed by a worker to see whether appearance of a culture has changed with repeated passaging in a process of culturing a stem cell maintaining an undifferentiated state, or to see whether there is a change between lots in a process of culturing a stem cell maintaining an undifferentiated state in a plurality of lots, for example.

Modification Example 1 of Third Embodiment

In the third embodiment, a flow of processing executed when data about the i-th passage culture is selected as reference data in Step S1001 is described.

The present invention is not limited thereto, and cell image data about two or more cell cultures may be selected as reference data. In that case, an average of a plurality of first evaluation values corresponding to the pieces of reference data may be subtracted from the first evaluation value corresponding to the evaluation target data, to thereby calculate the second evaluation value in Step S1004.

<Non-Transitory Storage Medium>

A non-transitory storage medium storing according to the present invention is a non-transitory storage medium storing a program for causing a computer to execute the cell image analysis method according to the present invention described above.

Figure 11:
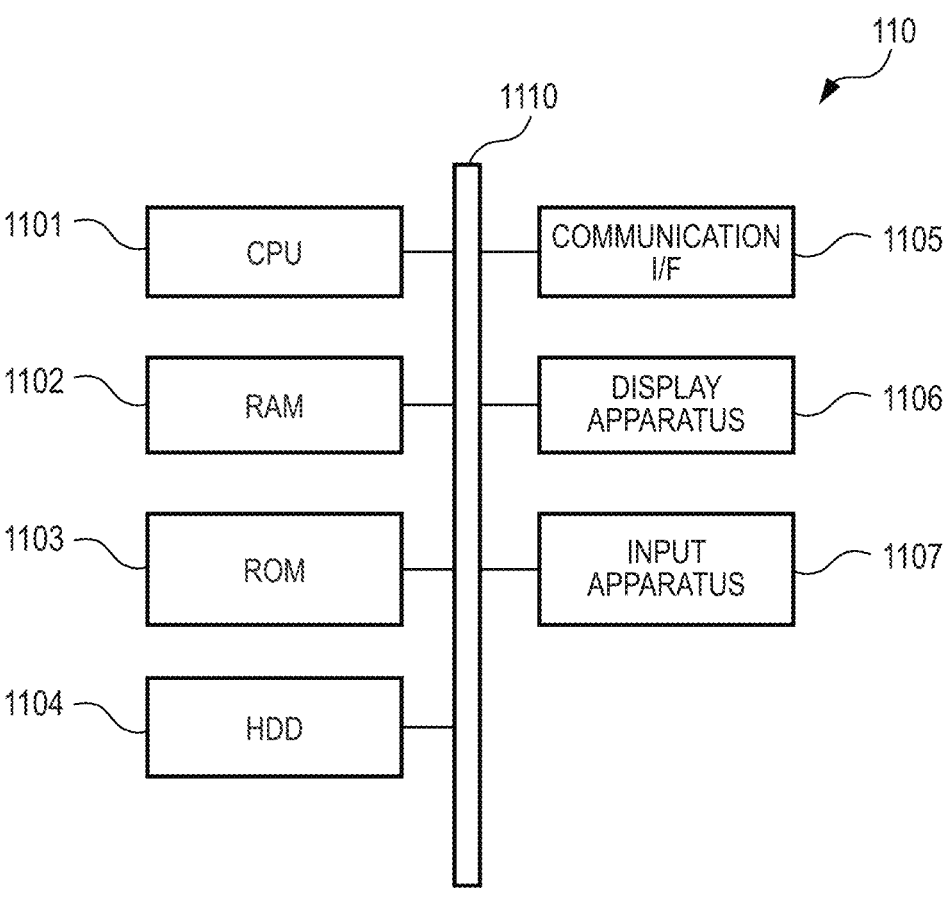
FIG. 11 is a diagram for illustrating a configuration of an information processing system in which a program stored in a non-transitory storage medium according to the present invention is executable.

FIG. 11 is a block diagram for illustrating a hardware configuration example of an information processing system 110 in which the program stored in the non-transitory storage medium according to the present invention is executable.

The information processing system 110 has functions of a computer. For example, the information processing system 110 may be configured unitarily with a desktop personal computer (PC), a laptop PC, a tablet PC, or a smartphone, for example.

The information processing system 1110 includes, in order to implement functions as a computer which performs arithmetic operation and storage, a central processing unit (CPU) 1101, a random-access memory (RAM) 1102, a read-only memory (ROM) 1103, and a hard disk drive (HDD) 1104. The information processing system 1110 also includes a communication interface (I/F) 1105, a display device 1106, and an input device 1107. The CPU 1101, the RAM 1102, the ROM 1103, the HDD 1104, the communication I/F 1105, the display device 1106, and the input device 1107 are connected to each other via a bus 1110. The display device 1106 and the input device 1107 may be connected to the bus 1110 via a drive device (not shown) for driving those devices.

In FIG. 11, the various components forming the information processing system 110 are illustrated as an integrated device, but a part of the functions of those components may be implemented by an external device. For example, the display device 1106 and the input device 1107 may be external devices different from the components implementing the functions of the computer including such as the CPU 1101.

The CPU 1101 performs predetermined operations in accordance with programs stored in, for example, the ROM 1103 and the HDD 1104, and also has a function of controlling each component of the information processing system 110. The RAM 1102 is built from a volatile storage medium, and provides a temporary memory area required for the operations of the CPU 1101. The ROM 1103 is built from a non-volatile storage medium, and stores required information such as programs to be used for the operations of the information processing system 110. The HDD 1104 is a storage device which is built from a non-volatile storage medium, and which stores information on the number of individual independent separate compartments and positions thereof and fluorescence intensities, for example.

The communication I/F 1105 is a communication interface based on a standard such as Wi-Fi (trademark) or 4G, and is a module for communicating to and from another device. The display device 1106 is, for example, a liquid crystal display or an organic light emitting diode (OLED) display, and is used for displaying moving images, still images, and characters, for example. The input device 1107 is, for example, a button, a touch panel, a keyboard, or a pointing device, and is used by a user to operate the information processing system 110. The display device 1106 and the input device 1107 may be integrally formed as a touch panel.

The hardware configuration illustrated in FIG. 11 is an example, and devices other than the illustrated devices may be added, or a part of the illustrated devices may be omitted. Further, a part of the devices may be substituted with another device having the same function. Moreover, a part of the functions may be provided by another device via a network, and the functions for implementing the embodiments may be shared and implemented by a plurality of devices. For example, the HDD 1104 may be substituted with a solid state drive (SSD) which uses a semiconductor element, such as a flash memory, or may be substituted with cloud storage.

Figure 12:
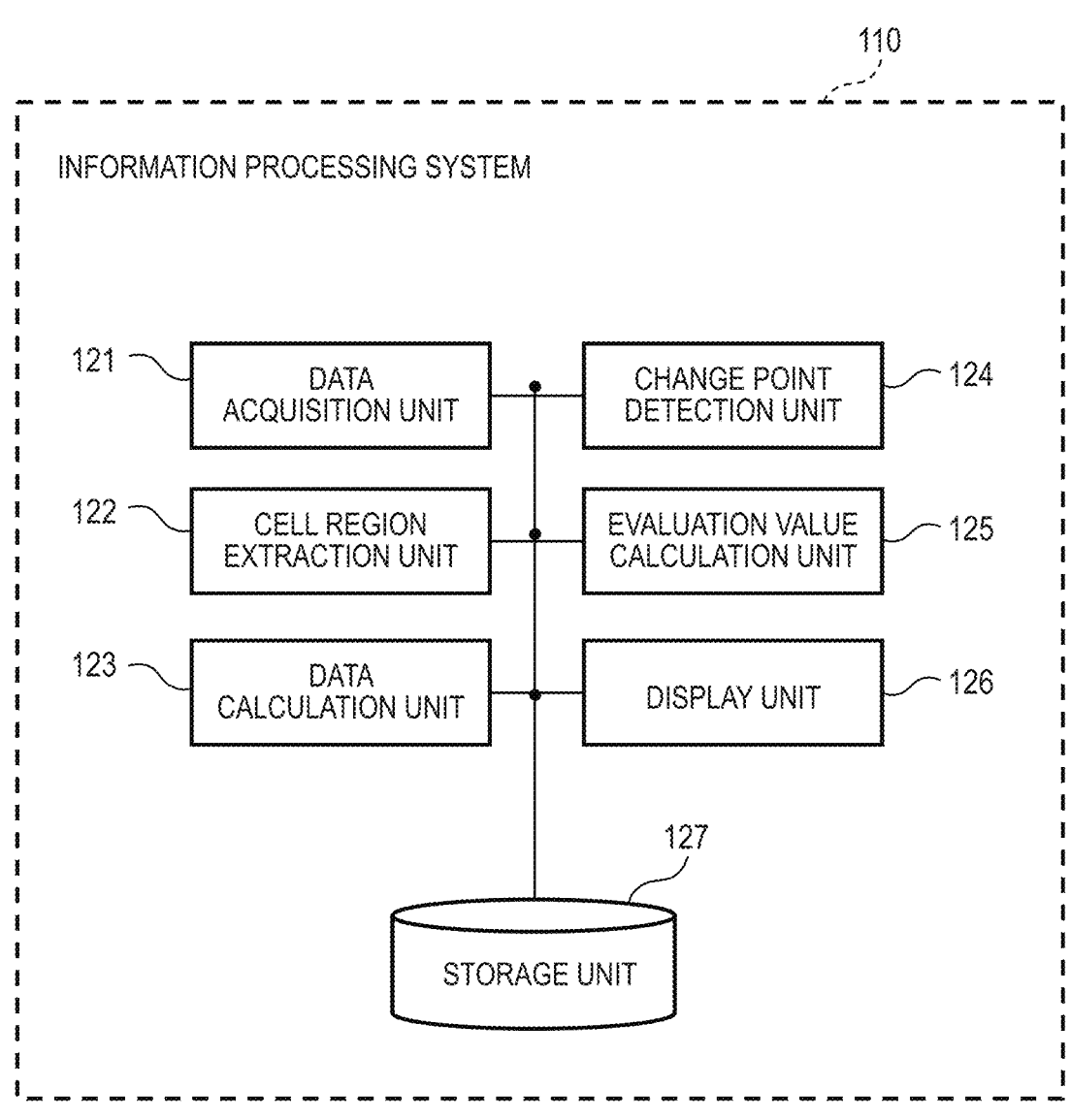
FIG. 12 is a function block diagram of the information processing system illustrated in FIG. 11.

FIG. 12 is a function block diagram of the information processing system 110. The information processing system 110 includes a data acquisition unit 121, a cell region extraction unit 122, a data calculation unit 123, a change point detection unit 124, an evaluation value calculation unit 125, a display unit 126, and a storage unit 127.

The evaluation value calculation unit 125 may be omitted from the information processing system 110 when, for example, the information processing system 110 executes the cell image analysis method described in the first embodiment.

The CPU 1101 implements functions of the data acquisition unit 121, the cell region extraction unit 122, the data calculation unit 123, the change point detection unit 124, and the evaluation value calculation unit 125 by loading the program stored in the ROM 1103 or another place onto the RAM 1102 and executing the program. The CPU 1101 also implements a function of the display unit 126 by controlling the display apparatus 1106. The CPU 1101 implements a function of the storage unit 127 as well by controlling the HDD 1104.

The information processing system 110 may further have a function of controlling operation of the cell culture observation apparatus described above and an incubator for performing cell culture, and the like in accordance with a predetermined program.

According to the present invention, the cell image analysis method which enables accurate grasping of the change point of the colony in cell culture is provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-019604, filed Feb. 10, 2022, and Japanese Patent Application No. 2022-143150, filed Sep. 8, 2022, which are hereby incorporated by reference herein in their entirety.

What is claimed is:

1. A cell image analysis method comprising:
   a data acquisition step of acquiring cell image data generated in time series in cell culture;
   a cell region extraction step of extracting, from the cell image data, a plurality of cell regions where one cell region corresponds to one of a plurality of colonies;
   a data calculation step of calculating, for each of the plurality of cell regions, one out of an area of the each of the plurality of cell regions in time series, a length of a circumference of the each of the plurality of cell regions in time series, a radius of the each of the plurality of cell regions in time series, and a diameter of the each of the plurality of cell regions in time series; and
   a change point detection step of detecting, based on the one out of the area of the each of the plurality of cell regions in time series, length of the circumference of the each of the plurality of cell regions in time series, the radius of the each of the plurality of cell regions in time series, and the diameter of the each of the plurality of cell regions in time series calculated in the data calculation step, a change point, which is timing of a change in a state of each of the plurality of colonies,
   wherein the change point is timing at which a rate change obtained from the one out of the area of the each of the plurality of cell regions in time series, length of the circumference of the each of the plurality of cell regions in time series, the radius of the each of the plurality of cell regions in time series, and the diameter of the each of the plurality of cell regions in time series changes from an increase trend to a decrease trend.

2. The cell image analysis method according to claim 1, wherein the data acquisition step includes acquiring cell image data generated in time series in cell culture in which an undifferentiated state is maintained.

3. The cell image analysis method according to claim 1, wherein the cell region extraction step includes determining which of the plurality of cell regions correspond to the identical colony between pieces of the cell image data acquired at different time points along the time series, based on at least one selected from centroids of the plurality of cell regions and degrees of overlapping among the plurality of cell regions.

4. The cell image analysis method according to claim 1, wherein the cell region extraction step includes determining whether a colony present in a piece of the cell image data acquired at a time point A in the time series is a colony formed as a result of joining of two or more colonies present in a piece of the cell image data acquired at a time point B which precedes the time point A in the time series, and, when the colony present in the piece of the cell image data of the time point A is determined to be a colony formed as a result of joining of two or more colonies present in the piece of the cell image data of the time point B, excluding the colony present in the piece of the cell image data of the time point A as a target from which the cell region is to be extracted.

5. The cell image analysis method according to claim 1, wherein the cell region extraction step includes determining whether a colony that is a target from which the cell region is to be extracted is in contact with at least one selected from an outer circumference of a culture vessel and an outer circumference of an image pickup field, and, when it is determined that the colony is in contact, excluding the colony determined to be in contact as the target from which the cell region is to be extracted.

6. The cell image analysis method according to claim 1, wherein when, with respect to pieces of data about sizes of the cell regions calculated for the cell regions corresponding to one identical colony, a value acquired at one certain time point in the time series has an amount of change equal to or more than a predetermined value from a reference value which is based on a value acquired at at least one other time point, the data calculation step includes excluding the pieces of data about sizes of the cell regions calculated for the cell regions corresponding to the one identical colony.

7. The cell image analysis method according to claim 1, wherein the change point is detected based on one of a length of time of the cell culture or the size of the each of the plurality of cell regions, and on a rate of change in size of the each of the plurality of cell regions.

8. The cell image analysis method according to claim 1, further comprising approximating a relationship between one of a length of time of the cell culture or the size of the each of the plurality of cell regions and a rate of change in size of the each of the plurality of cell regions as a polynomial model, and determining a local maximum point in the polynomial model as the change point.

9. The cell image analysis method according to claim 1, wherein the change point is timing at which a rate of change in area of the each of the plurality of cell regions changes from increase to decrease.

10. The cell image analysis method according to claim 1, further comprising an evaluation value calculation step of calculating, based on the change point, an evaluation value for a culture condition used in the cell culture.

11. The cell image analysis method according to claim 10, wherein the evaluation value calculation step includes calculating, for at least one type of data selected from a time, the size of the each of the plurality of cell regions, and a rate of change in size of the each of the plurality of cell regions, the at least one type of data corresponding to the change point in each of the plurality of colonies, at least one type of value selected from an average value, a standard deviation, a CV value, and a median value.

12. The cell image analysis method according to claim 10, wherein the cell image data includes data about a plurality of cell cultures cultured under culture conditions different from one another, and wherein the evaluation value calculation step includes calculating a first evaluation value for each of the plurality of cell cultures, and calculating, based on the first evaluation value, a second evaluation value about the culture conditions different from one another.

13. A non-transitory storage medium storing a program for causing a computer to execute the cell image analysis method of claim 1.

14. A cell image analysis method comprising:
a data acquisition step of acquiring cell image data generated in time series in cell culture;

a cell region extraction step of extracting, from the cell image data, a plurality of cell regions where one cell region corresponds to one of a plurality of colonies;

a data calculation step of calculating, for each of the plurality of cell regions, data about a size of the each of the plurality of cell regions; and a change point detection step of detecting, based on the data about the size of the each of the plurality of cell regions calculated in the data calculation step, a change point, which is timing of a change in a state of each of the plurality of colonies, wherein the cell region extraction step includes determining whether a colony that is a target from which the cell region is to be extracted is in contact with at least one selected from an outer circumference of a culture vessel and an outer circumference of an image pickup field, and, when it is determined that the colony is in contact, excluding the colony determined to be in contact as the target from which the cell region is to be extracted.

15. A cell image analysis method comprising:
a data acquisition step of acquiring cell image data generated in time series in cell culture;

a cell region extraction step of extracting, from the cell image data, a plurality of cell regions where one cell region corresponds to one of a plurality of colonies;

a data calculation step of calculating, for each of the plurality of cell regions, data about a size of the each of the plurality of cell regions;

a change point detection step of detecting, based on the data about the size of the each of the plurality of cell regions calculated in the data calculation step, a change point, which is timing of a change in a state of each of the plurality of colonies; and a cell processing timing determination step of determining timing of a cell processing based on the change point detected.

16. The cell image analysis method according to claim 15, wherein the cell processing is passage of a cell.

17. A cell image analysis method comprising:
a data acquisition step of acquiring cell image data generated in time series in cell culture;

a cell region extraction step of extracting, from the cell image data, a plurality of cell regions where one cell region corresponds to one of a plurality of colonies;

a data calculation step of calculating, for each of the plurality of cell regions, data about a size of the each of the plurality of cell regions; and a change point detection step of detecting, based on the data about the size of the each of the plurality of cell regions calculated in the data calculation step, a change point, which is timing of a change in a state of each of the plurality of colonies, wherein the timing of the change is timing a local maximum value of the data about the size of the each of the plurality of cell regions in time series and is identified as timing at which after timing at which the local maximum value is obtained, the data about the size of the each of the plurality of cell regions decrease from the local maximum value.

* * * * *